United States Patent
Ozdener

(10) Patent No.: US 10,908,147 B2
(45) Date of Patent: Feb. 2, 2021

(54) METHODS OF IDENTIFYING MODULATORS OF OLFACTORY RECEPTORS

(71) Applicant: Monell Chemical Senses Center, Philadelphia, PA (US)

(72) Inventor: Mehmet Hakan Ozdener, Springfield, PA (US)

(73) Assignee: Monell Chemical Senses Center, Philadelphia, PA (US)

( * ) Notice: Subject to any disclaimer, the term of this patent is extended or adjusted under 35 U.S.C. 154(b) by 1001 days.

(21) Appl. No.: 15/104,825

(22) PCT Filed: Dec. 15, 2014

(86) PCT No.: PCT/US2014/070365
§ 371 (c)(1),
(2) Date: Jun. 15, 2016

(87) PCT Pub. No.: WO2015/095062
PCT Pub. Date: Jun. 25, 2015

(65) Prior Publication Data
US 2016/0313305 A1  Oct. 27, 2016

Related U.S. Application Data

(60) Provisional application No. 61/916,423, filed on Dec. 16, 2013.

(51) Int. Cl.
| | | |
|---|---|---|
| *A01K 67/027* | (2006.01) | |
| *G01N 33/50* | (2006.01) | |
| *C12N 5/0793* | (2010.01) | |
| *C07K 14/705* | (2006.01) | |
| *G01N 33/68* | (2006.01) | |

(52) U.S. Cl.
CPC ..... *G01N 33/5041* (2013.01); *A01K 67/0275* (2013.01); *A01K 67/0278* (2013.01); *C07K 14/705* (2013.01); *C12N 5/062* (2013.01); *G01N 33/6872* (2013.01); *A01K 2217/052* (2013.01); *A01K 2217/206* (2013.01); *A01K 2227/105* (2013.01); *A01K 2267/0393* (2013.01); *C12N 2510/00* (2013.01); *C12N 2840/203* (2013.01); *G01N 2333/705* (2013.01)

(58) Field of Classification Search
None
See application file for complete search history.

(56) References Cited

U.S. PATENT DOCUMENTS

| | | |
|---|---|---|
| 5,993,778 A | 11/1999 | Firestein et al. |
| 6,670,317 B2 | 12/2003 | Severns et al. |
| 7,374,878 B2 | 5/2008 | Stryer et al. |
| 7,488,599 B2 | 2/2009 | Rawson et al. |
| 8,030,068 B2 | 10/2011 | Rawson et al. |
| 8,460,925 B2 | 6/2013 | Rawson et al. |
| 2002/0132273 A1 | 9/2002 | Stryer et al. |
| 2008/0299586 A1 | 12/2008 | Han et al. |
| 2011/0151483 A1 | 6/2011 | Zuker et al. |
| 2016/0313305 A1* | 10/2016 | Ozdener ............. C07K 14/705 |

FOREIGN PATENT DOCUMENTS

| | | |
|---|---|---|
| JP | 2008/503220 A | 2/2008 |
| WO | WO-2001/005833 | 1/2001 |
| WO | WO-2001/068805 | 9/2001 |
| WO | WO-2006002161 A2 | 1/2006 |
| WO | WO-2006/044594 | 4/2006 |

OTHER PUBLICATIONS

Peterlin, et al., The state of the art of odorant receptor deorphanization: a report from the orphanage. J Gen Physiol. May 2014;143(5):527-42. doi: 10.1085/jgp.201311151. Epub Apr. 14, 2014.

Chaudhari, et al, "The cell biology of taste." J Cell Biol. Aug. 9, 2010;190(3):285-96. doi: 10.1083/jcb.201003144, Published Aug. 9, 2010.

Murrell and Hunter. An Olfactory Sensory Neuron Line, Odora J. Neurosci., Oct. 1, 1999, 19(19):8260-8270). Published in print Oct. 1, 1999.

Lindemann, Taste reception. Physiol. Rev., Jul. 1996;76(3):719-66.

Figueroa, et al., Large-scale investigation of the olfactory receptor space using a microfluidic microwell array. Lab Chip. May 7, 2010;10(9):1120-7. doi: 10.1039/b920585c. Epub Feb. 10, 2010.

Harris, et al., Endocytic Function, Glycosaminoglycan Specificity, and Antibody Sensitivity of the Recombinant Human 190-kDa Hyaluronan Receptor for Endocytosis (HARE)* J Biol Chem. Aug. 27, 2004;279(35):36201-9. Epub Jun. 18, 2004.

Minic, et al., Functional expression of olfactory receptors in yeast and development of a bioassay for odorant screening. FEBS J. Jan. 2005;272(2):524-37. First published: Dec. 21, 2004.

(Continued)

*Primary Examiner* — Michael D Burkhart
(74) *Attorney, Agent, or Firm* — Howson & Howson, LLP; Mary E. Bak

(57) ABSTRACT

Described herein are mammalian taste papillae cells, cell lines, and cell membranes, methods, and kits for identifying agents, including ligands for olfactory receptors and enhancers and blockers thereof, that bind to or modulate the activity of olfactory receptors on mammalian taste papillae cells.

18 Claims, 37 Drawing Sheets

(56) References Cited

OTHER PUBLICATIONS

Saito, et al., RTP family members induce functional expression of mammalian odorant receptors. Cell. Nov. 24, 2004;119(5):679-91. Published: Nov. 23, 2004.
Trimmer, et al., High-throughput Analysis of Mammalian Olfactory Receptors: Measurement of Receptor Activation via Luciferase Activity. J Vis Exp. Jun. 2, 2014;(88). doi: 10.3791/51640.
Zhang et al., Evaluating cell-surface expression and measuring activation of mammalian odorant receptors in heterologous cells. Nat Protoc. 2008;3(9):1402-13. doi: 10.1038/nprot.2008.120. Published: Aug. 14, 2008.
User Guide. Growth and Maintenance of Flp-In™ Cell Lines. Revision 3.0 Life technologies. 20 pages, Oct. 16, 2013.
Stenesh, Dictionary of Biochemistry and Molecular Biology. p. 187. May 1, 1992.
Malik, et al., Mammalian Taste Cells Express Functional Olfactory Receptors. Chem Senses. May 29, 2019;44(5):289-301. doi: 10.1093/chemse/bjz019. Published: Apr. 24, 2019.
Response filed on Apr. 3, 2019 in reply to the Oct. 3, 2018 Office Action in corresponding Japanese Application No. 2016-539900, with correspondence dated Mar. 28, 2019 to the agent providing instruction regarding filing of this response as an unofficial translation.
Response filed on Dec. 19, 2017 in reply to the Jun. 7, 2017 Office Action in corresponding Chinese Application No. 201480072908.1, filed Jul. 12, 2016, with correspondence dated Dec. 1, 2017 to the agent providing instruction regarding filing of this response as well as correspondence dated Jul. 13, 2017 from agent providing suggestions, as an unofficial translation.
Response filed on Jun. 5, 2018 in reply to the Mar. 23, 2018 Office Action dated issued in corresponding Chinese Application No. 201480072908.1, with correspondence dated May 25, 2018 to the agent providing instruction regarding filing of this response as an unofficial translation.
Tsuboi, A. et at., Two highly homologous mouse odorant receptors encoded by tandemly-linked MOR29A and MOR29B genes respond differently to phenyl ethers, European Journal of Neuroscience, Nov. 2010, 33(2):205-213.
Oka, Y. et al., Odorant Receptor Map in the Mouse Olfactory Bulb: In Vivo Sensitivity and Specificity of Receptor-Defined Glomeruli, Neuron, Dec. 2006, 52(5):857-869.
Fleischmann, A. et al., Mice with a "Monoclonal Nose": Perturbations in an Olfactory Map Impair Odor Discrimination, Neuron, Dec. 2008, 60(6):1068-1081.
Levasseur, G. et al., Ligand-specific dose-response of heterologously expressed olfactory receptors, European Journal of Biochemistry, Jul. 2003, 270(13):2905-2912.
Ko, H. J. and Park, T. H., Functional analysis of olfactory receptors expressed in a HEK-293 cell system by using cameleons, Journal of Microbiology and Biotechnology, Jun. 2007, 17(6):928-933.
Wu, C. et al., Piezoelectric biosensor based on olfactory receptor expressed in a heterologous cell system for drug discovery, IFMBE Proceedings—7th Asian-Pacific Conference on Medical and Biological Engineering, Apr. 2008, 19:313-316.
Office Action dated Jun. 7, 2017 in corresponding Chinese Application No. 201480072908.1, filed Jul. 12, 2016.
Partial Supplementary European Search Report dated Jun. 29, 2017 in corresponding European Application No. 14871908.1, filed Jun. 15, 2016.
Extended European Search Report dated Sep. 22, 2017 in corresponding European Application No. 14871908.1, filed Jun. 15, 2016.
International Search Report dated Mar. 16, 2015 in corresponding International Patent Application No. PCT/US14/70365, filed Dec. 15, 2014.
Written Opinion dated Mar. 16, 2015 in corresponding International Patent Application No. PCT/US14/70365, filed Dec. 15, 2014.
International Preliminary Report on Patentability dated Jun. 30, 2016 in corresponding International Patent Application No. PCT/US14/70365, filed Dec. 15, 2014.
Office Action dated Mar. 23, 2018 issued in corresponding Chinese Application No. 201480072908.1.
Informal translation of Cite No. 1, the Office Action dated Mar. 23, 2018 in the counterpart Chinese Patent Application No. 201480072908.1, provided as correspondence from the Chinese agent with confidential information redacted.
Response filed on Apr. 9, 2018 in reply to Search Report and Communication issued in corresponding European Application No. 14871908.1.
Kenzo Kurihara, Receptor mechanisms of taste and olfaction, Oyobuturi, 1991, vol. 60, Issue 7, pp. 682-690, Released Feb. 5, 2009, Online ISSN 2188-2290, Print ISSN 0369-8009, https://doi.org/10.11470/oubutsu1932.60.682, https://www.jstage.jst.go.jp/article/oubutsu1932/60/7/60_7_682/_article/-char/en with an informal English translation of the Japanese abstract provided by Google Chrome.
Decision to Grant Patent dated Aug. 28, 2019 in the corresponding Japanese Patent Application No. 2016-539900.
Communication under Rule 71(3) EPC showing intention to grant dated Sep. 18, 2018 in the corresponding European Patent Application No. 14871908.1.
Response filed on Jul. 12, 2018 in reply to the May 15, 2018 Communication pursuant to Article 94(3) EPC in the corresponding European Patent Application No. 14871908.1.
Communication pursuant to Article 94(3) EPC dated May 15, 2018 in the corresponding European Patent Application No. 14871908.1.
Fleischmann et al., Mice with a "monoclonal nose": perturbations in an olfactory map impair odor discrimination. Neuron, 2008, 60(6):1068-1081. Dec. 26, 2008.
Bozza et al., Odorant receptor expression defines functional units in the mouse olfactory system. J Neurosci. Apr. 15, 2002;22(8):3033-43. Published in print Apr. 15, 2002.
Breer and Boekhoff, Odorants of the same odor class activate different second messenger pathways. Chemical Senses, vol. 16, Issue 1, Feb. 1, 1991, pp. 19-29. Published: Feb. 1, 1991.
Budanova et al. Immunohistochemical detection of olfactory marker protein in tissues with ectopic expression of olfactory receptor genes. Biochemistry (Moscow) Supplement Series A: Membrane and Cell Biology. Mar. 2010, vol. 4, Issue 1, pp. 120-123.
Donnelly, et al, The cleavage activities of aphthovirus and cardiovirus 2A proteins. J. Gen. Virol., 78(Pt 1):13-21 (Jan. 1997).
Durzynski L, et al. Olfactory-like receptor cDNAs are present in human lingual cDNA libraries. Biochem Biophys Res Commun. Jul. 22, 2005;333(1 ):264-72. Available online May 31, 2005.
Furler, S., et al, Recombinant AAV vectors containing the foot and mouth disease virus 2A sequence confer efficient bicistronic gene expression in cultured cells and rat substantia nigra neurons. Gene Ther., 8(11):864-873 (Jun. 2001).
Gaudin JC, et al. Mouse orthologs of human olfactory-like receptors expressed in the tongue. Gene. Oct. 15, 2006;381:42-8. Epub Jun. 22, 2006.
Gaudin JC; et al. New GPCRs from a human lingual cDNA library. Chem Senses. Nov. 2001;26(9): 1157-66. Published: Nov. 1, 2001.
Hiroi, et al. Hedonic taste in *Drosophila* revealed by olfactory receptors expressed in taste neurons. PLoS One. Jul. 9, 2008;3(7):e2610. pp. 1-9. Published: Jul. 9, 2008.
Klump H., et al., Retroviral vector-mediated expression of HoxB4 in hematopoietic cells using a novel coexpression strategy. Gene Ther., 8(10): 811-817 (May 2001).
Malnic et al., The human olfactory receptor gene family. PNAS, 2004, 101(8): 2584-2589. Published first Feb. 13, 2004.
Olender. et al., Update on the olfactory receptor (OR) gene superfamily. Human Genomics, 2008, 3(1): 87-97. Published online Sep. 1, 2008.
Ozdener et al., Characterization and long-term maintenance of rat taste cells in culture. Chem Senses. Mar. 2006;31(3):279-90. Epub Feb. 1, 2006.
Ozdener et al., Culture and maintenance of taste cells in vitro. In Vitro Cellular & Developmental Biology-Animal. Sep. 2011, 47(8): 513-14. Epub Jul. 1, 2011.
Ozdener et al., Characterization of human fungiforin papillae cells in culture. Chem Senses. Sep. 2011;36(7):601-12. doi: 10.1093/chemse/bjr012. Epub Apr. 6, 2011.

(56) References Cited

OTHER PUBLICATIONS

Restrepo et al., Odorant-regulated Ca2+ gradients in rat olfactory neurons. 1993, J. Gen. Physiol., 102(5):907-924. Nov. 1, 1993.
Schroeder and Neacile, FLIPR: A New Instrument for Accurate, High Throughput Optical Screening. J. Biomol. Screening. vol. 1, No. 2, p. 75-80 (1996). First Published Mar. 1, 1996.
Wu, et al, Receptor-transporting Protein 1 Short (R TP 1 S) Mediates Translocation and Activation of Odo rant Receptors by Acting through Multiple Steps, J. Biol. Chem., 2012, 287(26):22287-94. Epub May 8, 2012.
Zhang and Firestein, The olfactory receptor gene superfamily of the mouse Nature Neurosci., 2002, 5(2): 124-133. Published: Jan. 22, 2002.
Zozulya et al., The human olfactory receptor repertoire. Genome Biol., 2001, 2(6): research0018.1-0018.2. Epub Jun. 1, 2001.
Mus musculus olfactory reeptor 54 (Olfr544), mRNA. NCBI Reference Sequence: NM_020289.2. webpage <https://www.ncbi.nlm.nih.gov/nuccore/NM_020289.2> retrieved Dec. 3, 2018, last updated May 24, 2018.
*Homo sapiens* olfactory receptor family 7 subfamily D member 4 (OR7D4), mRNA. NCBI Reference Sequence: NM_001005191.2. webpage <https://www.ncbi.nlm.nih.gov/nuccore/NM_001005191.2> retrieved Dec. 3, 2018, last updated Jun. 25, 2018.
Office Action dated Oct. 3, 2018 issued in corresponding Japanese Application No. 2016-539900.
Informal translation of the Office Action dated Oct. 3, 2018 issued in corresponding Japanese Application No. 2016-539900, provided by the Japanese agent.

\* cited by examiner

PLC-b2  Overlay

GFP

METHODS OF IDENTIFYING MODULATORS OF OLFACTORY RECEPTORS

CROSS-REFERENCE TO RELATED APPLICATIONS

This application is a national stage of International Patent Application No. PCT/US2014/070365, filed Dec. 15, 2014, which claims the benefit of the priority of U.S. Provisional Patent Application No. 61/916,423, filed Dec. 16, 2013, which applications are incorporated herein by reference.

BACKGROUND

Chemical communication is widely used among various organisms to obtain information required for life from the environment. Olfaction and taste are each a form of chemoreception. Taste and olfaction systems are each tuned to a unique set of chemicals in the outside world, and their corresponding sensory spaces are mapped in different areas in the brain. In vertebrates, each taste cell is sensitive to at least one taste modality according to the combination of taste receptors it expresses: T2R receptors for bitterness, T1R receptors for sweet and umami, and PKD2L1 ion channels for sourness. In vertebrates, olfactory receptors constitute the largest subfamily of G protein-coupled receptors with up to a thousand members expected in mammalian species. This diversity represents the molecular basis allowing the olfactory system to discriminate among thousands of odorants.

Although taste and smell are separate sensory systems in most animals, some organisms have one chemical sense. The snake, for example, uses its tongue as part of its system of perception. When the tongue is flicked out into the air, receptors on the tongue pick up minuscule chemical particles, which are perceived as scent. When the tongue is retracted into its sheath, the tips of the tongue fit neatly into the Jacobson's organ, sending the chemical information that has been gathered through the organ and to the brain, where the information is quickly processed and analyzed so that the snake can act promptly on it. In *Drosophila* and in some other insects, taste neurons expressing ectopic olfactory receptors can sense odors.

Progress in understanding mammalian olfactory sensation has been significantly hampered by the lack of a model system for use in identifying modulators of olfactory receptors. Provided herein are methods for identifying modulators of olfactory receptors based on the finding of functional expression of olfactory receptors in mammalian taste papillae cells.

SUMMARY

Provided herein are methods for identifying a modulator of an olfactory receptor. The methods involve detecting the activity of the olfactory receptor of a taste papillae cell or taste papillae cell membrane in the presence and absence of a test agent; and identifying the test agent as a modulator of the olfactory receptor if the receptor activity increases or decreases in the presence of the test agent relative to the activity of the olfactory receptor in the absence of said test agent.

Also provided herein are methods for identifying an olfactory receptor ligand. Such methods involve contacting a taste papillae cell or taste papillae cell membrane comprising an olfactory receptor with a test agent; and detecting the activity of the olfactory receptor. The method may further involve detecting the presence or absence of an olfactory receptor ligand based upon the activity of the olfactory receptor.

Further provided herein are methods for identifying an enhancer of an olfactory receptor ligand by contacting a taste papillae cell or taste papillae cell membrane comprising an olfactory receptor with a test agent in the presence of the olfactory receptor ligand; and detecting the activity of the olfactory receptor in the presence and absence of the test agent, wherein the test agent is an enhancer of the olfactory receptor ligand if the activity of the olfactory receptor in the presence of the test agent is increased relative to the activity of the olfactory receptor in the absence of the test agent.

Also provided herein are methods for identifying a blocker of an olfactory receptor ligand by contacting a taste papillae cell or taste papillae cell membrane comprising an olfactory receptor with a test agent in the presence of the olfactory receptor ligand; and detecting the activity of the olfactory receptor in the presence and absence of the test agent, wherein the test agent is a blocker of the olfactory receptor ligand if the activity of the olfactory receptor in the presence of the test agent is decreased relative to the activity of the olfactory receptor in the absence of the test agent. In some embodiments, the test agent competes with the olfactory receptor ligand for binding to the olfactory receptor.

In some embodiments of the methods provided herein, activity of the olfactory receptor is detected by contacting the taste papillae cell or cell membrane with the test agent. Activity of the olfactory receptor may be detected by determining intracellular $Ca^{2+}$ levels or by detecting a reporting agent.

The taste papillae cell or cell membrane employed in accordance with the methods may be mammalian, for example human or murine. In some embodiments of the disclosed methods, the taste papillae cell is an immortalized taste papillae cell or the taste papillae cell membrane is obtained from an immortalized taste papillae cell. In other embodiments, the taste papillae cell is a primary taste papillae cell or the taste papillae cell membrane is obtained from a primary taste papillae cell.

The taste papillae cell or cell membrane employed in accordance with the methods may be circumvallate taste papillae cell or cell membrane, a fungiform taste papillae cell or cell membrane, or a foliate taste papillae cell or cell membrane.

The test agent employed in accordance with the methods provided herein may be a natural agent or a synthetic agent or an odiferous molecule.

In some embodiments of the methods, the olfactory receptor is a mammalian olfactory receptor, for example, a human olfactory receptor or murine olfactory receptor. The olfactory receptor may be a heterologous olfactory receptor.

Further embodied herein are kits for identifying an agent as an odorant. Such a kit includes a mammalian taste papillae cell or cell membrane and instructions. The kit may also include a reporting agent that enables detection of activity of the olfactory receptor in response to the agent. The taste papillae cell or taste papillae cell membrane may be mammalian, for example but not limited to, human or murine. The taste papillae cell or cell membrane may be a primary or immortalized taste papillae cell or cell membrane. The taste papillae cell or cell membrane may be a circumvallate taste papillae cell or cell membrane, a fungiform taste papillae cell or cell membrane, or a foliate taste papillae cell or cell membrane. In some embodiments the taste papillae cell or cell membrane comprises a mammalian olfactory receptor, for example, a human olfactory receptor or murine olfactory receptor. In some embodiments the taste papillae cell or cell membrane comprises a heterologous olfactory receptor.

Also provided are kits for identifying an agent as blocker or enhancer of an olfactory receptor ligand including a mammalian taste papillae cell or cell membrane and a known odorant. The kit may also include instructions. The kit may also include a reporting agent that enables detection of activity of the olfactory receptor in response to the agent. The taste papillae cell or taste papillae cell membrane may be mammalian, for example but not limited to, human or murine. The taste papillae cell or cell membrane may be a primary or immortalized taste papillae cell or cell membrane. The taste papillae cell or cell membrane may be a circumvallate taste papillae cell or cell membrane, a fungiform taste papillae cell or cell membrane, or a foliate taste papillae cell or cell membrane. In some embodiments the taste papillae cell or cell membrane comprises a mammalian olfactory receptor, for example, a human olfactory receptor or murine olfactory receptor. In some embodiments the taste papillae cell or cell membrane comprises a heterologous olfactory receptor.

Further provided herein are mammalian taste papillae cells, or cell membranes thereof, that express an olfactory receptor operably linked to a reporting agent. The cell may be a primary cell or an immortalized cell. The cell is preferably mammalian, for example but not limited to, human or murine. The cell may be a circumvallate taste papillae cell, a fungiform taste papillae cell, or a foliate taste papillae cell. The olfactory receptor is preferably a mammalian olfactory receptor, more preferably a human or murine olfactory receptor. In some embodiments, the olfactory receptor is a heterologous olfactory receptor. Also provided are kits comprising the aforesaid mammalian taste papillae cells or cell membranes and instructions.

Also provided are mammalian taste papillae cell lines that express an olfactory receptor operably linked to a reporting agent. The cell line is preferably mammalian, for example but not limited to, human or murine. The cell line may be derived from a circumvallate taste papillae cell, a fungiform taste papillae cell, or a foliate taste papillae cell. The olfactory receptor is preferably a mammalian olfactory receptor, more preferably a human or murine olfactory receptor. In some embodiments, the olfactory receptor is a heterologous olfactory receptor. Also provided are kits comprising the aforesaid mammalian taste papillae cell lines and instructions.

The cells, cell membranes, kits, and related methods of use are more fully discussed herein.

BRIEF DESCRIPTION OF THE DRAWINGS

FIG. 1A shows transmission images of corresponding fields. FIG. 1B shows expression of GFP in circumvallate papillae. FIG. 1C shows the overlap of GFP and circumvallate papillae. Images were arranged and minimally adjusted for contrast and brightness using LCS software (Leica Microsystems Inc.) and Adobe Photoshop® elements 2.0 (Adobe Systems Inc.). Scale bar=25 µM.

FIG. 2A shows transmission images of corresponding fields. FIG. 2B shows expression of GFP in circumvallate papillae. FIG. 2C shows the overlap of GFP and circumvallate papillae. Images were arranged and minimally adjusted as described above for FIGS. 1A-1C.

FIG. 3A shows transmission images of corresponding fields. FIG. 3B shows expression of GFP in circumvallate papillae. FIG. 3C shows the overlap of GFP and circumvallate papillae. Images were arranged and minimally adjusted as described above for FIGS. 1A-1C.

FIG. 4A shows transmission images of corresponding fields. FIG. 4B shows expression of GFP in circumvallate papillae. Images were arranged and minimally adjusted as described above for FIGS. 1A-1C.

FIGS. 12A and 12D show transmission images of cultured human taste papillae cells, in the absence or presence, respectively, of OR8D1 specific peptide. Cultured human taste papillae cells (HBO) stained with OR8D1 antibodies in the absence (FIG. 12B) and presence of its specific peptide (FIG. 12E) are shown. FIG. 12B demonstrates the presence of OR8D1 expression in subgroup of cultured human taste papillae cells though preincubation of OR8D1 antibodies with its specific peptide resulted in complete removal of OR8D1 specific immunostaining (FIG. 12E). FIGS. 12C and 12F show transmission images of the nuclei of cultured human taste papillae cells, in the absence or presence, respectively, of OR8D1 specific peptide.

FIG. 29A shows light transmission of cultured mOR-EUG-GFP mouse taste cells. FIG. 29B shows the cells of FIG. 29A expressing GFP. FIG. 29C shows the cells of FIG. 29A in overlay. These figures indicates that eugenol responsive cells express GFP indicating the presence of Eugenol receptor on the cultured mouse taste cells which responded to eugenol.

FIG. 30A shows light transmission of cultured mOR-EUG-GFP mouse taste cells. FIGS. 30B and 30C show the cultured mouse taste cells expressing GFP. These figures indicate that eugenol responsive cells express GFP indicating the presence of Eugenol receptor on the cultured mouse taste cells which responded to eugenol.

DETAILED DESCRIPTION OF ILLUSTRATIVE EMBODIMENTS

Figure 1A:
FIGS. 1A to 1C show transmission images of I7 olfactory receptors in circumvallate taste papillae of mOR-I7-GFP mice. mOR-I7-GFP transgenic mice demonstrated the expression of green fluorescent protein (GFP) in circumvallate taste papillae. Images were acquired with a LEICA® TCS-SP2 confocal laser scanning microscope.
Figure 1B:
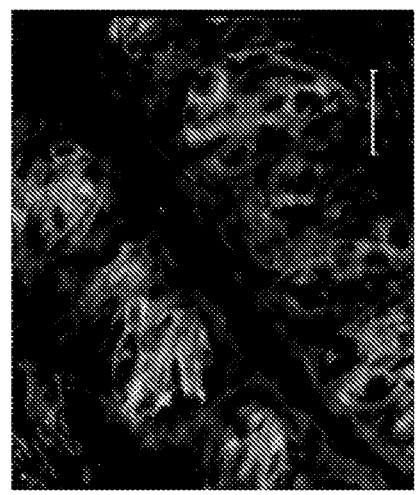
Figure 1C:
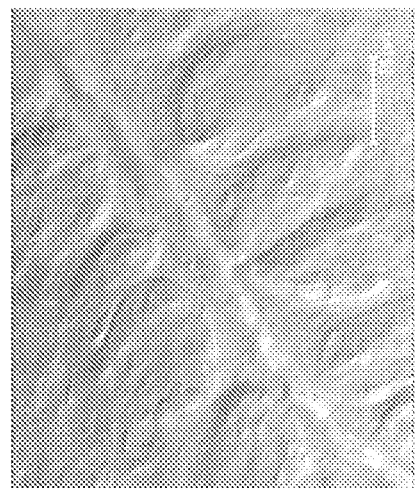

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like. Various embodiments in the specification are presented using "comprising" language, which is inclusive of other components or method steps. When "comprising" is used, it is to be understood that related embodiments include descriptions using the "consisting of" terminology, which excludes other components or method steps, and "consisting essentially of" terminology, which excludes any components or method steps that substantially change the nature of the embodiment or invention.

The term "about" as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

As used herein, the term "competes for binding" is used in reference to a first agent with an activity which binds to the same substrate as does a second agent with an activity. The efficiency (e.g., kinetics or thermodynamics) of binding by the first agent may be the same as or greater than or less than the efficiency of substrate binding by the second agent. For example, the equilibrium binding constant ($K_D$) for binding to the substrate may be different for the two agents.

The term "primary cell" as used herein refers to a non-transformed, non-immortalized cell isolated directly from tissue.

As used herein, the term "reporter gene" refers to a gene encoding a protein that may be assayed. "Reporter genes or molecules" include genes encoding fluorescent agents, chemiluminescent agents, chromogenic agents, quenching agents, radionucleotides, enzymes, substrates, cofactors, inhibitors, and other moieties known in the art. "Reporter molecules" in certain embodiments, can generate a measurable signal. Examples of reporter genes include, but are not limited to, luciferase, green fluorescent protein (e.g., tauGFP), yellow fluorescent protein, cyan fluorescent protein, red fluorescent protein, yellow-red fluorescent protein, chloramphenicol acetyltransferase, beta-galactosidase, alkaline phosphatase, and horse radish peroxidase.

As used herein, the term "response," when used in reference to an assay, refers to the generation of a detectable signal (e.g., accumulation of reporter protein, increase in ion concentration, accumulation of a detectable chemical product).

The phrase "taste papillae cell" as used herein refers to a taste basal cell and/or a cell that expresses one or more taste receptors and responds to one or more tastant stimuli (as determined, for example, by monitoring intracellular calcium levels and/or electrophysiological data). In some embodiments, the taste papillae cell expresses one or more biomarkers of a taste papillae cell (e.g., phospholipase-beta 2 and/or gustducin). A taste basal cell expresses one or more stem cell markers (e.g., cytokeratin 8 (CK8), HES1, HES6, Sox2, mash1, etc) and can differentiate into taste cell type (e.g., Type I, Type II, or Type III).

The term "test agent" refers to any natural or synthetic chemical entity, pharmaceutical, drug, foodstuff, and the like. For example, a test agent may be a food, a pharmaceutical, a component or breakdown product of a food or pharmaceutical, or a contaminant of a food or pharmaceutical.

Described herein are cells, cell membranes, methods, and kits that serve to further the understanding of olfactory coding by providing a model system for identification of cognate olfactory receptor ligands and enhancers and blockers thereof. The described cells, cell membranes, methods, and kits provide numerous research, diagnostic, therapeutic, drug and foodstuff screening applications. For example, the described cells, cell membranes, methods, and kits permit identification and characterization of olfactory receptor ligands responsible for health conditions and olfactory responses. The cells, cell membranes, methods, and kits thus also provide means for identification of ligands that allow manipulation of olfactory responses (e.g. for the control of perceived scents).

Taste Papillae Cells and Cell Membranes

Provided herein are taste papillae cells that functionally express one or more olfactory receptors (ORs). In some embodiments, one or more of the olfactory receptors expressed by the taste papillae cell are native to the cell. Also provided are taste papillae cells that have been modified to include one or more polynucleotides encoding an OR (i.e., heterologous expression, e.g., recombinantly expressed). Methods of transforming cells to include a polynucleotide encoding an olfactory receptor can be used to produce the modified cells described herein, as would be understood by those skilled in the art (see, e.g., U.S. Pat. No. 7,488,599, incorporated herein by reference). In preferred embodiments, the taste papillae cells and cell membranes are mammalian, including but not limited to bird, mouse, rat, rabbit, monkey, ape, or human and preferably are human or murine.

Also provided are cell membranes of the described taste papillae cells that functionally express one or more olfactory receptors.

An olfactory receptor is a G-protein coupled receptor (GPCR) that is bound by an odorant to initiate a cascade of intracellular signaling events resulting in a change in the intracellular calcium level. Olfactory receptors expressed in the cell membranes of olfactory receptor neurons are responsible for the detection of odor molecules. Activated olfactory receptors are the initial player in a signal transduction cascade which ultimately produces a nerve impulse which is transmitted to the brain. These receptors are members of the class A rhodopsin-like family of GPCRs. Certain chaparone or accessory proteins are present in mammalian olfactory cells or in taste cells expressing ORs that facilitate their trafficking to the cell-surface membrane and ligand-induced responses, e.g., RTP1S. When heterologously expressed in cultured cells of non-olfactory origins, odorant receptor proteins are retained in the endoplasmic reticulum. Thus, cells, cell lines or cell membranes as described herein, which are not native taste cells containing an OR, must be modified to contain the accessory proteins like RTP1S to facilitate their trafficking to the cell-surface membrane and ligand-induced responses in heterologous cells (i.e., cells not naturally containing the OR or the accessory proteins. Alternatively, cells that naturally contain the accessory proteins can be modified to contain and express additional ORs as described herein, and using conventional transfection or other known cell modification techniques.

Functional olfactory receptor expression can be determined by any means known in the art (for example, by monitoring intracellular calcium levels and/or electrophysiological data). The olfactory receptor may be any mammalian olfactory receptor, including but not limited to an olfactory receptor obtained from a bird, mouse, rat, rabbit, monkey, ape, or human. The olfactory receptor is preferably human or murine. Examples of olfactory receptors are known to those skilled in the art and include, but are not limited to, human OR51L, OR5D18, OR8D1, OR2J2, OR2W1, OR10J5 and OR5P3; murine Olfr15, Olfr16, Olfr17, Olfr64, Olfr73, Olfr653, Olfr1519, Olfr749, Olfr1352, Olfr1079, Olfr1377, Olfr556, Olfr1341 Olfr1062, Olfr109, Olfr508, Olfr983, Olfr876, Olfr1104, Olfr168, Olfr429, Olfr167, Olfr151, and Olfr895; and fragments and derivatives thereof having the ability to effect a response induced by an odorant. See, e.g., Zhang and Firestein, Nature Neurosci., 2002, 5(2): 124-133; Malnic et al., PNAS, 2004, 101(8): 2584-2589; Olender et al., Human Genomics, 2008, 3(1): 87-97; Zozulya et al., Genome Biol., 2001, 2(6): research 0018.1-0018.2. Each of these references is incorporated herein by reference.

The taste papillae cells and cell membranes may be obtained from peripheral tissue such as tongue (see, e.g., U.S. Pat. No. 7,488,599, incorporated herein by reference), including foliate, fungiform, or circumvallate taste papillae cells or cell membranes thereof. The taste papillae cells and cell membranes for use in accordance with the methods and kits described herein may be primary or immortalized taste papillae cells or cell membranes obtained therefrom. Thus also provided herein are cell lines of mammalian taste papillae cells that express one or more olfactory receptors.

In some embodiments of the described taste papillae cells, cell lines, and cell membranes are modified so that the olfactory receptor gene or gene promoter is operably linked to a reporting agent. Exemplary murine olfactory receptor gene promoters include but are not limited to the eugenol promoter, the M71 promoter, and the I7 promoter, and Olfr15, Olfr16, Olfr17, Olfr64, Olfr73, Olfr653, Olfr1519, Olfr749, Olfr1352, Olfr1079, Olfr1377, Olfr556, Olfr1341 Olfr1062, Olfr109, Olfr508, Olfr983, Olfr876, Olfr1104, Olfr168, Olfr429, Olfr167, Olfr151, and Olfr895 promoters. Exemplary human promoters include but are not limited to those of olfactory receptor OR51L, OR5D18, OR8D1, OR2J2, OR2W1, OR10J5 and OR5P3. Suitable reporters are listed herein. In some embodiments, the sequence encoding the reporting agent is introduced with an internal ribosomal entry site (IRES). Such linkage allows detection of expression of the olfactory receptor. The selected promoter may be induced by appropriate means followed by detection of the reporting agent.

In one embodiment, taste cells are transiently transfected with olfactory receptor DNA operably linked to a suitable promoter and optional reporter gene and optionally chapparone DNA as discussed above. Methods employed for generation of the DNA sequences for such transfection are described in the art; see e.g., one of the publications above cited or Sambrook et al Molecular Cloning: A Laboratory Manual, Cold Spring Harbor Press, Cold Spring Harbor, N.Y. Selection of suitable promoters as described above, suitable olfactory receptor DNA, reporter sequences, as well as accessory DNA sequences to enable the cells to express the receptor. Such accessory sequences include RTP1S, M1 sequences (see, e.g., Wu, L et al, June 2012, "Receptor-transporting Protein 1 Short (RTP1S) Mediates Translocation and Activation of Odorant Receptors by Acting through Multiple Steps, J. Biol. Chem., 287(26):22287-94). Other useful sequences include internal ribozyme entry sites (IRES), e.g., the poliovirus internal ribosome entry sequence. Still others are known and available in the art. As an alternative to an IRES, the DNA can include sequences encoding a 2A peptide, which self-cleaves in a post-translational event. See, e.g., M. L. Donnelly, et al, J. Gen. Virol., 78 (Pt 1): 13-21 (January 1997); Furler, S., et al, Gene Ther., 8(11): 864-873 (June 2001); Klump H., et al., Gene Ther., 8(10): 811-817 (May 2001). Still other desirable sequences are spacer sequences of about 15-25 nucleic acids, or introns spaced between the promoter and the one or more operator sequences, as well as nuclear localization sequence (NLS). Additional regulatory sequences for inclusion in the DNA sequence include, without limitation, an enhancer sequence, a splice donor sequence and a splice acceptor sequence, a site for transcription initiation and termination, a ribosome binding site, an epitope tag, a Goldberg-Hogness "TATA" element, a restriction enzyme cleavage site, a selectable marker, origins of replication, polyadenylation sequences (e.g., BGH polyA, SV40 polyA), drug resistance markers (e.g., kanamycin resistance). All such elements may also be selected from among widely known sequences.

The DNA sequences are transfected into the cells by conventional routes, such as electroporation, delivery via suitable viruses or virus-like particles, e.g., AAV, or other known methodologies. The inventions described herein are not limited by the particular technique of transfection employed, nor by the selection of the components of the DNA sequences to be transfected. See, e.g., texts such as the various editions of Sambrook et al, Molecular Cloning: A Laboratory Manual, Cold Spring Harbor Press, Cold Spring Harbor, N.Y.

Methods of Use of the Described Taste Papillae Cells and Cell Membranes

The described taste papillae cells, cell lines, and cell membranes may be employed in methods for identifying ligands and modulators of olfactory receptors as provided herein. The ability of a test agent to bind to an olfactory receptor on the taste papillae cells, cell lines, and cell membranes can be accomplished, for example, by coupling the agent to a radioisotope or enzymatic label such that binding of the agent to the olfactory receptor can be determined by detecting the labeled agent in a complex. For example, test agents can be labeled with $^{125}$I, $^{35}$S, $^{14}$C, or $^{3}$H, either directly or indirectly, and the radioisotope detected by direct counting of radioemission or by scintillation counting. Alternatively, test agents can be enzymatically labeled with, for example, horseradish peroxidase, alkaline phosphatase, or luciferase, and the enzymatic label detected by determination of conversion of an appropriate substrate to product. The ability of a test agent to interact with an olfactory receptor with or without the labeling of any of the interactants also can be evaluated by any means known in the art.

In some embodiments, the methods for identifying an olfactory receptor ligand involve exposing a described taste papillae cell, cell line, or cell membrane expressing a functional olfactory receptor to a test agent followed by detection of olfactory receptor activity. Test agents that may be employed include but are not limited to any natural or synthetic chemical entity, pharmaceutical, drug, food stuff, and the like. For example, a test agent may be a food, a pharmaceutical, a component or breakdown product of a food or pharmaceutical, an odiferous molecule or composition (e.g., heptanal, acetophenone, lyral, eugenol, bitter mixture, Mix A, Mix B), or a contaminant of a food or pharmaceutical. If the test agent is a ligand specific for the olfactory receptor, a change in olfactory receptor activity will be detectable.

In some embodiments, the taste papillae cells, cell lines, or cell membranes as described herein can be used in a second messenger assay that monitors signal transduction following activation of the olfactory receptor (e.g., measurement of intracellular $Ca^{+2}$ levels or cAMP levels). In a second messenger assay, the cells or cell membranes are contacted with an agent or plurality of agents (e.g., from a combinatorial library) and assayed for the presence or absence of a response. In some embodiments, the second messenger assays detect or measure fluorescent signals from reporter molecules that respond to intracellular changes (e.g., $Ca^{2+}$ levels, membrane potential, pH, cAMP, $IP_3$, arachidonic acid release) as a result of stimulation of membrane receptors and ion channels. Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF). In general, cells or cell membranes are loaded with the reporter molecule prior to exposure to the test agent. Responses of the cells or cell membranes to treatment with the test agents can be detected by methods known in the art, including, but not limited to, fluorescence microscopy, confocal microscopy, flow cytometry, microfluidic devices, FLIPR systems. See, e.g., Schroeder and Neagle, J. Biomol. Screening 1:75 (1996), incorporated herein by reference, and plate-reading systems.

In other embodiments, the taste papillae cells and cell membranes can be used in reporter gene assays that monitor cellular responses at the transcription/translation level. For example, if the olfactory receptor gene or gene promoter is operably linked to a reporting agent (e.g., glutathione-S-transferase (GST), c-myc, 6-histidine (6xHis), green fluorescent protein (GFP), maltose binding protein (MBP), influenza A virus haemagglutinin (HA), β-galactosidase, and GAL4), expression or a change in expression of the reporting agent will be detectable.

The described taste papillae cells, cell lines, and cell membranes may be employed in methods of identifying a modulator of an olfactory receptor. In some embodiments, the methods involve measuring or detecting the activity of a functional olfactory receptor expressed by the described taste papillae cells, cell lines, or cell membranes in the presence and absence of a test agent. Test agents that may be employed include but are not limited to any natural or synthetic chemical entity, pharmaceutical, drug, food stuff, and the like. For example, a test agent may be a food, a pharmaceutical, a component or breakdown product of a food or pharmaceutical, an odiferous molecule or composition (e.g., heptanal, acetophenone, lyral, eugenol, bitter mixture, Mix A, Mix B), or a contaminant of a food or pharmaceutical. If the test agent is an olfactory receptor modulator, olfactory receptor activity will increase or decrease in the presence of the test agent relative to olfactory receptor activity in the absence of the test agent. In some embodiments, the taste papillae cells, cell lines, or cell membranes as described herein can be used in a second messenger assay that monitors signal transduction following activation of the olfactory receptor (e.g., measurement of intracellular $Ca^{+2}$ levels or cAMP levels). In other embodiments, the taste papillae cells can be used in reporter gene assays that monitor cellular responses at the transcription/translation level. For example, if the olfactory receptor gene or gene promoter is operably linked to a reporting agent (e.g., glutathione-S-transferase (GST), c-myc, 6-histidine (6xHis), green fluorescent protein (GFP), maltose binding protein (MBP), influenza A virus haemagglutinin (HA), β-galactosidase, and GAL4), expression or a change in expression of the reporting agent in the presence of the test agent relative to that in the absence of the test agent will be detectable.

In another embodiment, the described taste papillae cells, cell lines, and cell membranes may be employed in methods for identifying enhancers of an odorant or olfactory receptor ligand in accordance with the methods provided herein. Thus, in some embodiments, methods of identifying natural or synthetic agents that increase or enhance olfactory receptor activity in response to a known odorant or olfactory receptor ligand are provided. The described taste papillae cells, cell lines, and cell membranes may be employed in the methods for identifying enhancers of an odorant or olfactory receptor ligand provided herein. Thus, in some embodiments, methods for identifying an enhancer of an odorant or olfactory receptor ligand involve contacting a taste papillae cell, cell line, or cell membrane that expresses a functional olfactory receptor as described herein with a test agent in the presence of the odorant or olfactory receptor ligand; and measuring or detecting olfactory receptor activity in the presence and absence of the test agent. Test agents that may be employed include but are not limited to any natural or synthetic chemical entity, pharmaceutical, drug, food stuff, and the like. For example, a test agent may be a food, a pharmaceutical, a component or breakdown product of a food or pharmaceutical, an odiferous molecule or composition (e.g., heptanal, acetophenone, lyral, eugenol, bitter mixture, Mix A, Mix B), or a contaminant of a food or pharmaceutical. The test agent is an enhancer of the odorant or olfactory receptor ligand if the olfactory receptor activity in the presence of the test agent is increased relative to the olfactory receptor activity in the absence of the test agent. In some embodiments, the taste papillae cells, cell lines, or cell membranes as described herein can be used in a second messenger assay that monitors signal transduction following activation of the odorant receptor (e.g., measurement of intracellular $Ca^{+2}$ levels or cAMP levels). An increase in receptor activity as measured by the second messenger assay in the presence of the test agent relative to that in the absence of the test agent is indicative of an enhancer. In other embodiments, the taste papillae cells can be used in reporter gene assays that monitor cellular responses at the transcription/translation level. For example, if the olfactory receptor gene or gene promoter is operably linked to a reporting agent (e.g., glutathione-S-transferase (GST), c-myc, 6-histidine (6xHis), green fluorescent protein (GFP), maltose binding protein (MBP), influenza A virus haemagglutinin (HA), β-galactosidase, and GAL4), an increase in detection of the reporting agent in the presence of the test agent relative to that in the absence of the test agent is indicative of an enhancer.

The described taste papillae cells, cell lines, and cell membranes also may be employed in methods for identifying blockers of an odorant or olfactory receptor ligand in accordance with the methods provided herein. Thus, in some embodiments, methods of identifying natural or synthetic agents that decrease or reduce olfactory receptor activity in response to a known odorant or olfactory receptor ligand are provided. The described taste papillae cells, cell lines, and cell membranes may be employed in the methods for identifying blockers of an odorant or olfactory receptor ligand provided herein. Thus, in some embodiments, methods for identifying a blocker of an odorant or olfactory receptor ligand involve contacting a taste papillae cell, cell line, or cell membrane that expresses a functional olfactory receptor as described herein with a test agent in the presence of the odorant or olfactory receptor ligand; and measuring or detecting olfactory receptor activity in the presence and absence of the test agent. Test agents that may be employed include but are not limited to any natural or synthetic chemical entity, pharmaceutical, drug, food stuff, and the like. For example, a test agent may be a food, a pharmaceutical, a component or breakdown product of a food or pharmaceutical, an odiferous molecule or composition (e.g., heptanal, acetophenone, lyral, eugenol, bitter mixture, Mix A, Mix B), or a contaminant of a food or pharmaceutical. The test agent is a blocker of the odorant or olfactory receptor ligand if the olfactory receptor activity in the presence of the test agent is decreased relative to the olfactory receptor activity in the absence of the test agent. In some embodiments, the taste papillae cells, cell lines, or cell membranes as described herein can be used in a second messenger assay that monitors signal transduction following activation of the olfactory receptor (e.g., measurement of intracellular Ca+2 levels or cAMP levels). A decrease in receptor activity as measured by the second messenger assay in the presence of the test agent relative to that in the absence of the test agent is indicative of a blocker. In other embodiments, the taste papillae cells can be used in reporter gene assays that monitor cellular responses at the transcription/translation level. For example, if the olfactory receptor gene or gene promoter is operably linked to a reporting agent (e.g., glutathione-S-transferase (GST), c-myc, 6-histidine (6xHis), green fluorescent protein (GFP), maltose binding protein (MBP), influenza A virus haemagglutinin (HA), β-galactosidase, and GAL4), a decrease in detection of the reporting agent in the presence of the test agent relative to that in the absence of the test agent is indicative of a blocker. Kits Also provided herein are kits for identifying an agent or a plurality of agents as an odorant or a modulator of an olfactory receptor. In some embodiments, the kits provide a taste papillae cell, cell line, or cell membrane expressing one or more olfactory receptors and instructions. The kit also may include a reporting agent that allows detection of activity of the olfactory receptor.

Also provided herein are kits for identifying a test agent as a blocker or enhancer of an olfactory receptor ligand, wherein the kits include a taste papillae cell, cell line, or cell membrane expressing one or more olfactory receptors and a known odorant. In some embodiments, the kits for identifying a test agent as blocker or enhancer of an olfactory receptor ligand include instructions.

The taste papillae cell, cell line, or cell membrane provided with the kits described herein are preferably mammalian, including but not limited to bird, mouse, rat, rabbit, monkey, ape, or human, and preferably are human or murine. The one or more olfactory receptors expressed by the taste papillae cell, cell line, or cell membrane are mammalian including but not limited to bird, mouse, rat, rabbit, monkey, ape, or human and preferably is human or murine. In some embodiments, the olfactory receptor is native to the taste papillae cell or cell membrane. In some embodiments, the olfactory receptor is heterologous. By "heterologous" is meant that the olfactory receptor is either not native to the cell, or is native to the cell but occurs natively in a different position in the cell genome, or is expressed at a different level in the native cell than in a modified cell. In some embodiments, the one or more olfactory receptors expressed by the taste papillae cell, cell line, or cell membrane provided with the kit are operably linked to a reporting agent.

The taste papillae cell or cell membrane expressing one or more olfactory receptors may be a primary cell or an immortalized cell or a cell membrane thereof. In preferred embodiments, the taste papillae cell, cell line, or cell membrane is obtained from a peripheral tissue, preferably tongue tissue. The taste papillae cell, cell line, or cell membrane expressing one or more olfactory receptors may be a circumvallate taste papillae cell or circumvallate taste papillae cell membrane; a fungiform taste papillae cell or fungiform taste papillae cell membrane; or a foliate taste papillae cell or foliate taste papillae cell membrane.

The instructions may direct the user to use the kit in accordance with the methods described herein. In some embodiments, the olfactory receptor(s) are labeled with a reporting agent that enables detection of olfactory receptor activity following exposure of the cell, cell line, or cell membrane to a test agent.

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

REFERENCES

Each of Which is Incorporated Herein by Reference

1. Gaudin J C, et al. Mouse orthologs of human olfactory-like receptors expressed in the tongue. Gene. 2006 Oct. 15; 381: 42-8. Epub 2006 Jun. 22.
2. Durzyński L, et al Olfactory-like receptor cDNAs are present in human lingual cDNA libraries. Biochem Biophys Res Commun. 2005 Jul. 22; 333(1): 264-72.
3. Gaudin J C, et al. New GPCRs from a human lingual cDNA library. Chem Senses. 2001 November; 26(9): 1157-66.

The following examples are illustrative only, and do not limit the scope of the present invention.

EXAMPLE 1

Material and Methods

A. Generation of I7, M71 and Eugenol Transgenic Mice

Odorant (or olfactory) receptor (OR) properties of taste papillae cells were investigated by examining taste papillae of I7, M71 and Eugenol (EG) transgenic mice. In one embodiment, mOR-EG-GFP line was made using a transgene consisting of 3.0 kb upstream of the mOR-EG transcription start site followed by mOR-EG-IRES-gapEGFP ("mOR-EG-GFP"). The IRES sequence allows for coexpression of an OR with a reporter protein. (Oka et al., Neuron, 2006, 52: 857-859, incorporated herein by reference). In another embodiment, the GFP labeled M71 mouse line was generated by inserting an internal ribosome entry site (IRES) and the coding sequence for the fluorescent, axonal marker tauGFP (IRES-tauGFP) downstream of the M71 OR coding sequence, producing the M71-IRES-tauGFP (M71-G) mutation ("mOR-M71-GFP"). (Axel et al., Neuron, 2008, 60(6): 1068-1081, incorporated herein by reference). In still another embodiment, the GFP labeled I7 mouse line was generated by inserting an IRES-tauGFP downstream of the I7 OR coding sequence, generating I7-IRES-tauGFP ("mOR-I7-GFP"). (Bozza et al., J. Neurosci., 2002, 22(8): 3033-3043, incorporated herein by reference). The construct was microinjected into the pronuclei of fertilized eggs.

B. Establishment and Maintenance of Cultures of Human Fungiform Taste Papillae Cells The human fungiform papillae cells were cultured according to published protocols (Ozdener et al., Chem Senses. 2006 March; 31(3): 279-90; Ozdener et al., In Vitro Cellular & Developmental Biology—Animal. September 2011, 47(8): 513-14; each of which is incorporated herein by reference). Briefly, human fungiform taste papillae were removed and immediately placed into an isolation solution [26 mM NaHCO3, 2.5 mM NaH2PO4, 20 mM glucose, 65 mM NaCl, 20 mM KCl, and 1 mM ethylenediaminetetraacetic acid (EDTA)] followed by enzymatic digestion with pronase E and elastase. Digested fungiform papillae were then gently minced with a surgical razor and seeded on collagen type-1 coated coverslips and incubated at 36° C. in a humidified environment containing 5% $CO_2$. The human fungiform taste papillae were cultured in Iscove's Modified Dulbecco's medium containing 10% fetal bovine serum, 1:5 ratio of MCDB 153, and a triple cocktail of antibiotics (100 U/mL/100 µg/mL, penicillin/streptomycin, and 0.5 µg/mL fungizone). Human fungiform taste papillae cells have been maintained in culture for a period of more than 1 year without loss of viability and with retention of the molecular and biochemical properties of acutely isolated taste cells.

C. Culture of Mouse Taste Papillae Cells

Circumvallate and foliate papillae obtained from wild (m129), I7, M71 and Eugenol transgenic mice were isolated according to previously published procedure (Ozdener et al., 2006, cited above). Briefly, mouse taste papillae were removed by injecting the mixture of enzyme (pronase, 1 mg/ml Sigma and elastase 1 mg/ml Sigma) and immediately placed into an isolation solution followed by enzymatic digestion. Digested taste papillae tissue were then gently minced with a surgical razor and seeded on collagen type-1 coated coverslips and incubated at 36° C. in a humidified environment containing 5% $CO_2$.

D. Immunohistochemistry and Immunocytochemistry

Mouse circumvallate and foliate taste papillae tissue were fixed in 4% paraformaldehyde (PFA) in phosphate-buffered saline (PBS, pH 7.2) for 1 hour at room temperature and then cryoprotected by sequential immersions in 10%, 20% and 30% sucrose in PBS for 24 hours each. Sagittal sections of each papilla were cut at 10 µm on a Microm HM 500 OM cryostat. Tissue sections were thaw-mounted onto Superfrost Plus® slides and either directly observed for GFP expression or stained (described below) to localize coexpression of GFP and taste related molecules, phospholipase beta 2 (PLC-b2), or gustducin.

Cultured human fungiform taste papillae (HBO) cells (passage 4-5) were fixed with 4% PFA in PBS for 10 min at room temperature. Cells were blocked with 3% normal goat serum, 3% bovine serum albumin and 0.3% Triton X-100 in PBS for 30-60 minutes and then incubated with primary antibody (OR8D1, SantaCruz) overnight at 4° C. To determine specificity of this antibody, this antibody was pre-incubated with its specific peptide overnight at 4° C. (or 4-5 hours RT) and then cells were also subjected this antibody+peptide mixture overnight at 4° C.

For mouse taste papillae tissue, the primary antibodies were used at following dilutions: 1:500 (anti-α-gustducin SantaCruz, anti-PLC-β2 SantaCruz). This step was followed by incubation with secondary antibodies diluted in blocking buffer for 30 min at room temperature. The secondary antibodies were anti-rabbit IgG Alexa 635 (Molecular Probes, USA). After washing with PBS and water, coverslips were mounted using Vectashield® with DAPI (Vector Laboratories). Immunoreactive cells were counted in at least three fields at 20× magnification. Images were acquired with a Leica® TCS SP2 Spectral Confocal Microscope (Leica Microsystems Inc.). Excitation wavelengths used were 405 nm for GFP, and 633 nm for Alexa Fluor® 633 with emissions detected at appropriate wavelengths.

Leica® Scanware software was used to acquire confocal images by scanning unidirectionally at 1024×1024 pixel format with 3 lines and 2 frames averaging. Computer controlled digital zoom was used to increase magnification to a maximum of 2.3× with the 20× objective. Images were arranged and minimally adjusted for contrast and brightness using LCS software (Leica Microsystems Inc.) and Adobe Photoshop® elements 2.0 (Adobe Systems Inc.).

D. Affymetrix Analysis of RNA Array

RNA from cultured human fungiform taste papillae taste cells were obtained using standard techniques. Total RNA was processed for use on the microarray by using the Affymetrix GeneChip® kit (Affymetrix, Santa Clara, Calif.) according to the manufacturer's recommended protocols.

E. Calcium Imaging

Changes in intracellular calcium levels in response to stimuli were measured. Cultured human fungiform and mice taste papillae cells were seeded on 15 mm coverslips. Cells were loaded with 1 mM Fura-2 AM (Molecular Probes Inc.) in 10 mg/mL Pluronic® F127 (Molecular Probes Inc.) in modified Ringer solution for 1 hour at 36° C. Individual odors, bitter mixture [phenylthiocarbamide (PTC, 2 mM) and Denatonium (2 mM), Salicin (5 mM)]; and Mix A [cAMP-producing odors in rat biochemical assays (Breer and Boekhoff, 1991, Chem. Senses, 16(1): 19-29, and Restrepo et al., 1993, J. Gen. Physiol., 102:907-924); both of which are incorporated herein by reference] (100 mM): hedione, geraniol, phenylethyl alcohol, citralva, citronellal, and eugenol,]; and Mix B [IP3-producing odors in rat biochemical assays (Breer and Boekhoff, 1991 and Restrepo et al 1993)] (100 mM): lyral, lilial, triethylamine, ethyl vanillin, isovaleric acid, and phenylethyl amine]) was diluted in Ringer, which was prepared with pH adjusted to 7.2 and osmolality adjusted to 300 mmol/kg. A coverslip was placed into a p4 chamber system with the delivery and waste pipes attached to the chamber. This allowed for a stable and constant flow of liquid in and out of the chamber. The cells were visualized with an inverted florescence microscope using an excitation wavelength of 380 nm. Stimulus selection and delivery, focusing, and image acquisition were done using PTI software. Following image acquisition, regions of interest (ROIs) on the cells along with a background control region were selected to be measured for fluorescence ratios and intensity values. Cultured taste papillae cells were first washed for 1-3 min with Ringer, and then stimuli delivery was initiated. Each stimulus was delivered for 30 sec-1 min followed by an approximately 2 min wash out period with Ringer. Ratio data for the cells were subsequently analyzed on Excel to determine which cells had responded with a significant change in intracellular calcium. After calcium imaging, coverslips were fixed with 4% PFA for 10 min and washed 3× with PBS. Cells were observed for GFP specific signal either before or after calcium imaging under either fluorescence imaging microscope or confocal microscopy and for co-localization of the olfactory responsive specific cells.

EXAMPLE 2

Figure 2A:
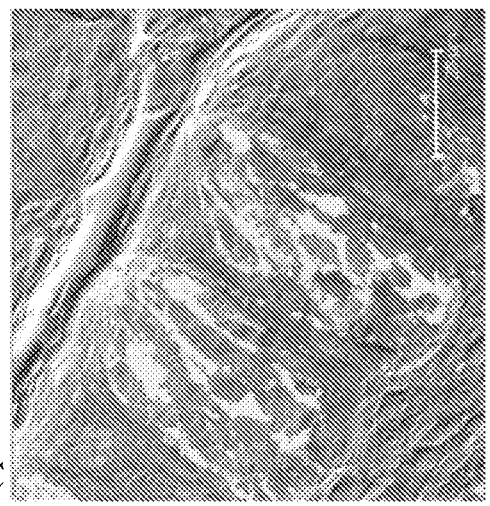
FIGS. 2A to 2C show transmission images of M71 olfactory receptors in circumvallate taste papillae of mOR-M71-GFP mice. mOR-M71-GFP transgenic mice demonstrated the expression of green fluorescent protein (GFP) in circumvallate taste papillae. Images were acquired with a LEICA® TCS-SP2 confocal laser scanning microscope.
Figure 2B:
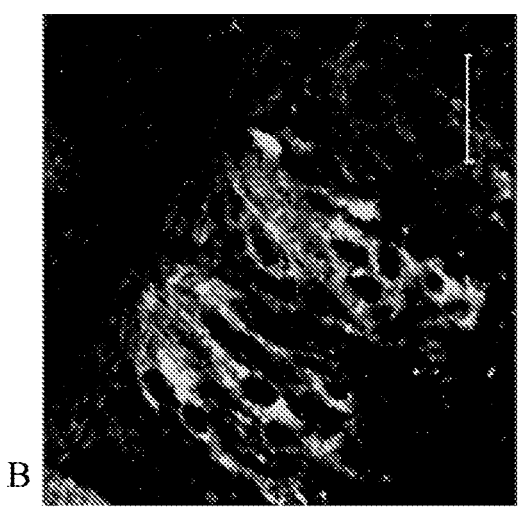
Figure 2C:
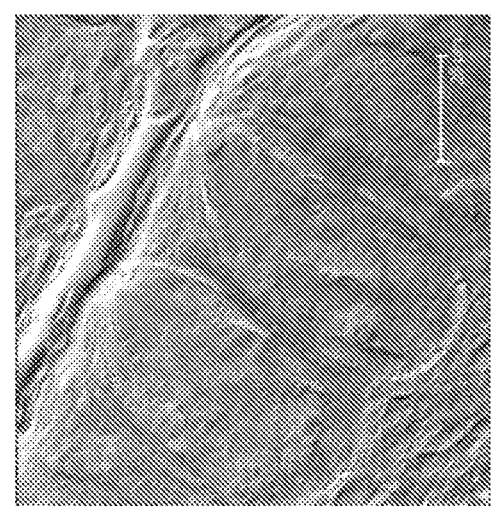
Figures 3A, 3B, 3C:
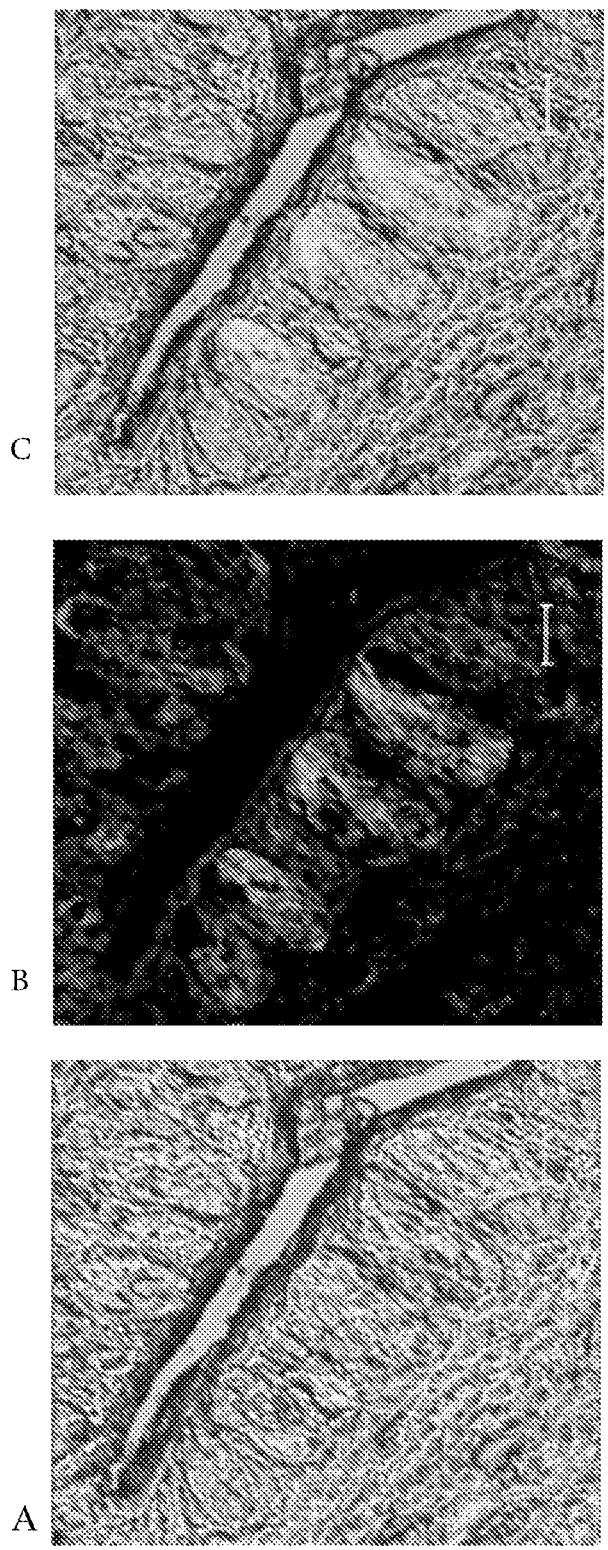
FIGS. 3A to 3C show transmission images of eugenol olfactory receptors in circumvallate taste papillae of mOR-EG-GFP mice. mOR-EG-GFP transgenic mice demonstrated the expression of GFP in circumvallate taste papillae. Images were acquired with a LEICA® TCS-SP2 confocal laser scanning microscope.
Figure 4A:
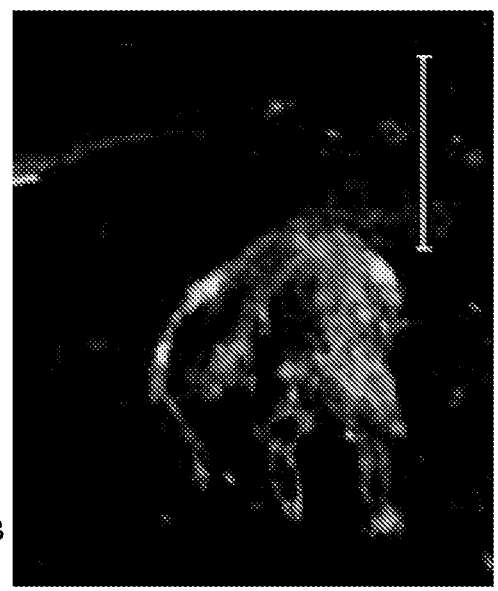
FIGS. 4A to 4B show transmission images of eugenol olfactory receptors in circumvallate taste papillae of mOR-EG-GFP mice. mOR-EG-GFP transgenic mice demonstrated the expression of GFP in circumvallate taste papillae. Images were acquired with a LEICA® TCS-SP2 confocal laser scanning microscope.
Figure 4B:
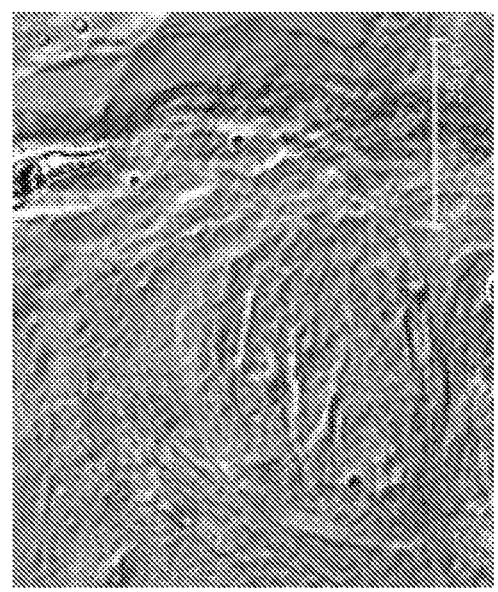
Figures 5A, 5B, 5C, 5D:
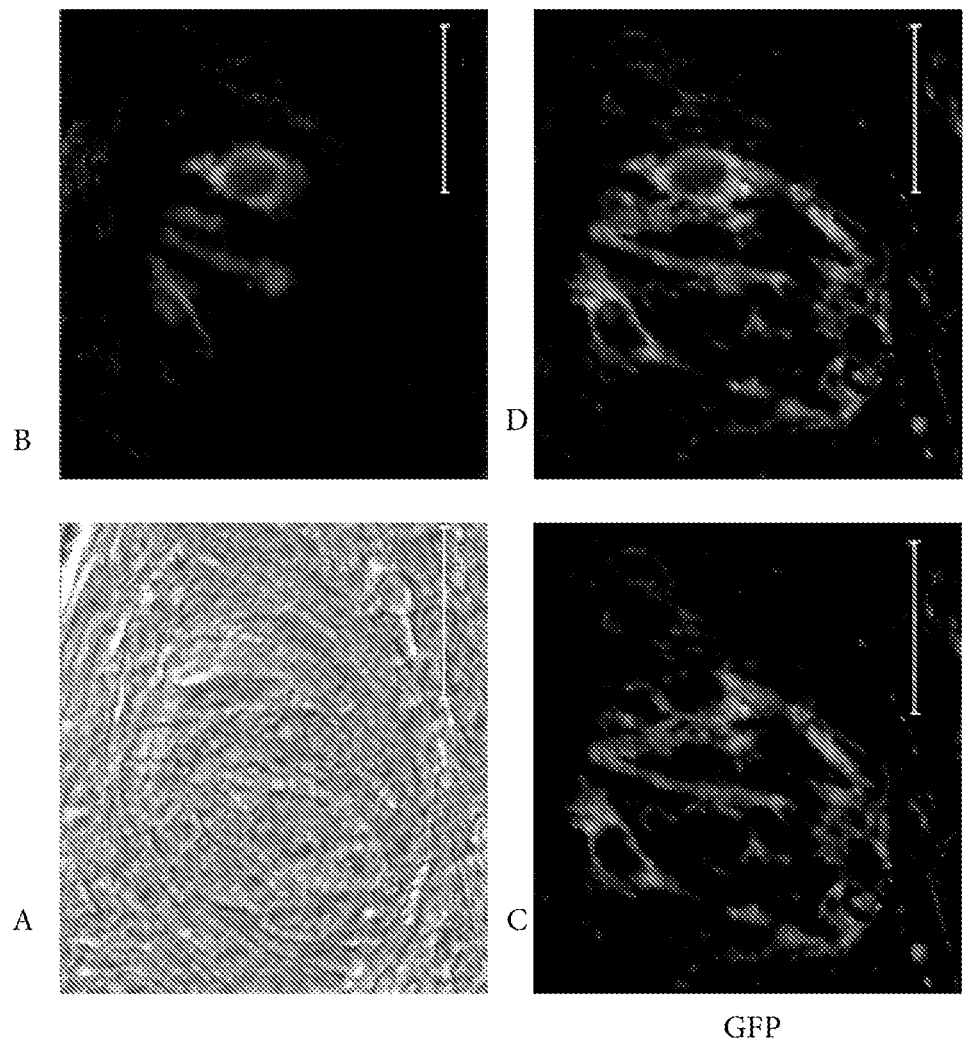
FIGS. 5A to 5D are transmission images of co-localization of PLC-b2 (A, B) and GFP (C, D) in circumvallate papillae of mOR-I7-GFP mice.
Figures 6A, 6B, 6C, 6D:
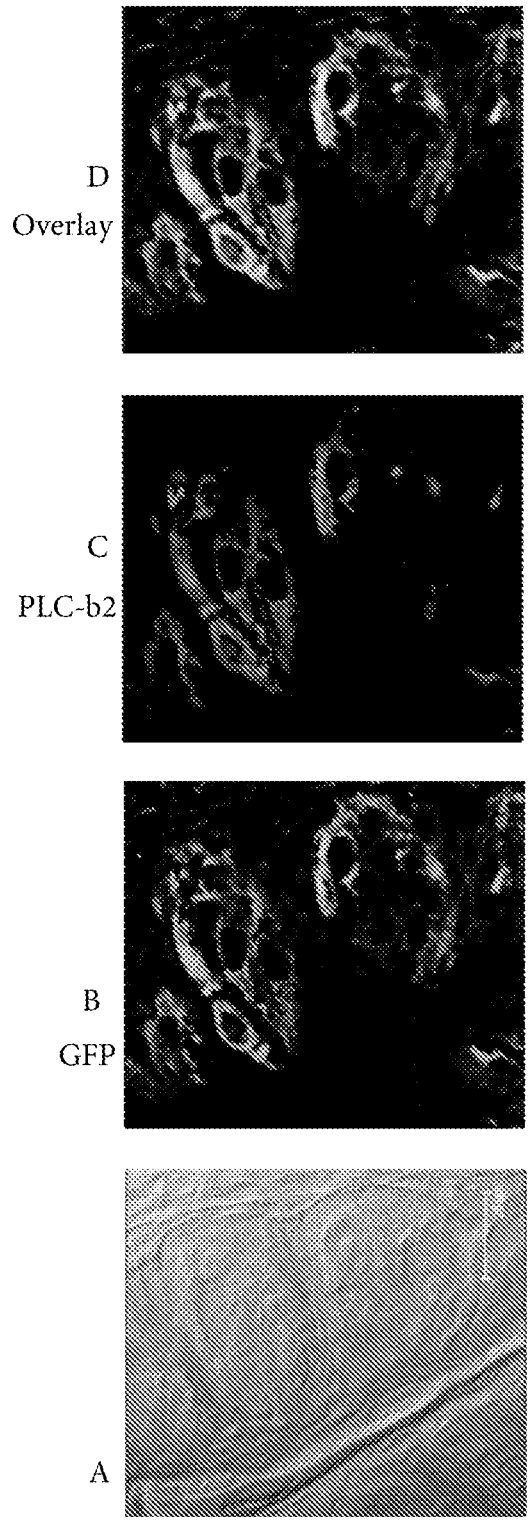
FIGS. 6A to 6D are transmission images showing co-localization of PLC-b2 (FIG. 6C) and GFP (FIG. 6B) in circumvallate papillae of mOR-M71-GFP mice. Unstained (FIG. 6A) and overlay (FIG. 6D) are also shown.
Figures 7A, 7B, 7C, 7D:
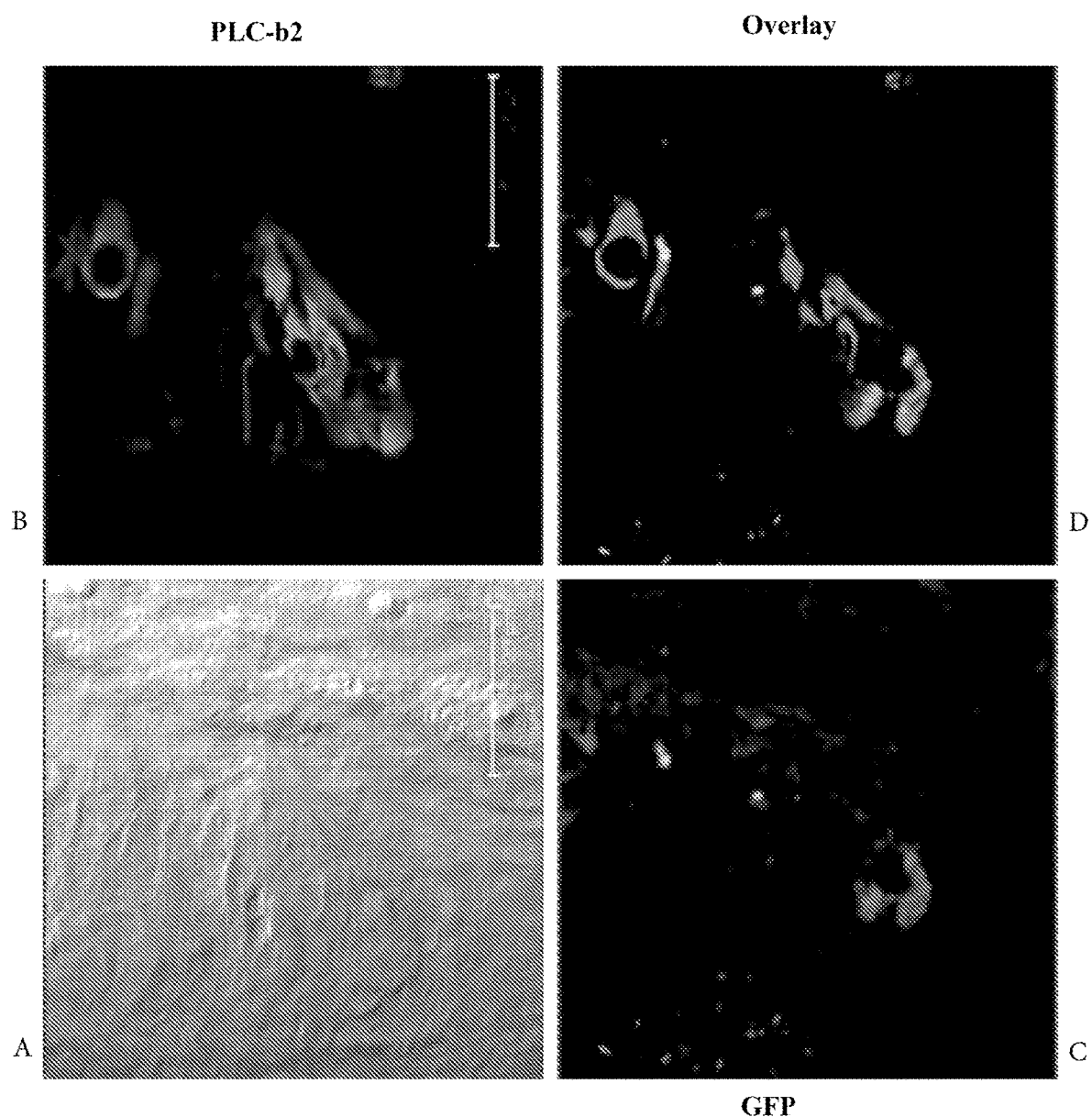
FIGS. 7A to 7D illustrate co-localization of PLC-b2 (7B) and GFP (7C) in circumvallate papillae of mOR-EG-GFP mice. Transmission images of overlay (7D) and unstained (7A) are also shown.
Figures 8A, 8B, 8C, 8D:
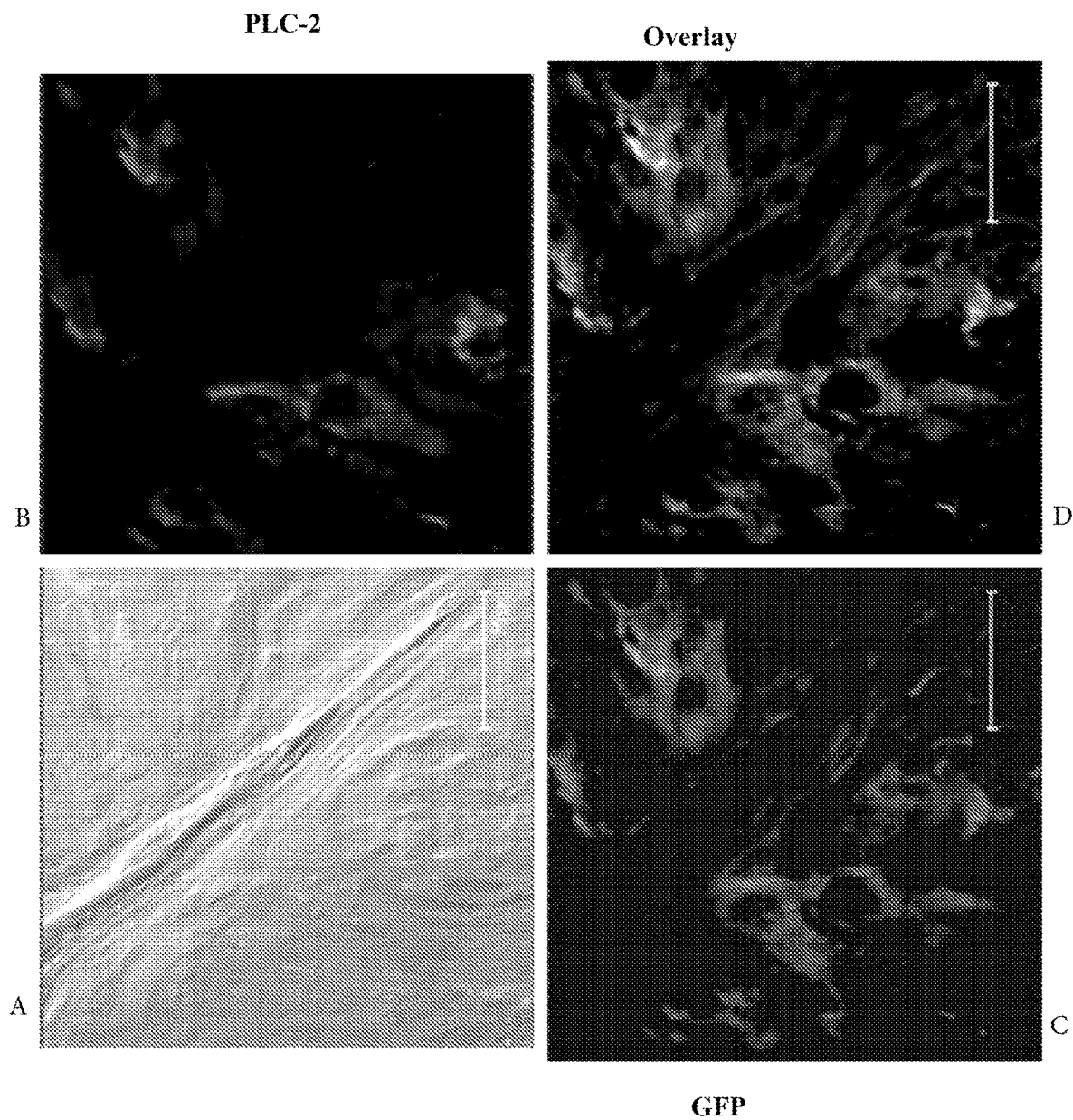
FIGS. 8A to 8D are transmission images showing co-localization of gustducin (8B) and GFP (8C) in circumvallate papillae of mOR-M71-GFP mice. Normal (8A) and overlay (8D) are also shown.
Figure 9A:
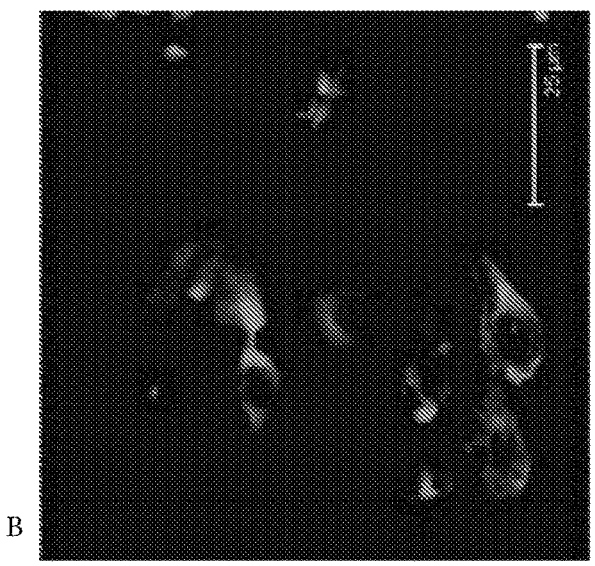
FIG. 9A to 9D are transmission images showing co-localization of gustducin (9B) and GFP (9C) in circumvallate papillae of mOR-EG-GFP. Normal (9A) and overlay (9D) are also shown.
Figure 9B:
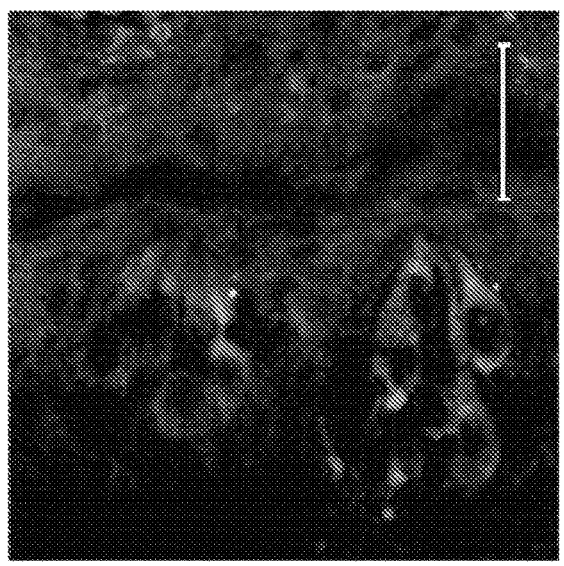
Figure 9C:
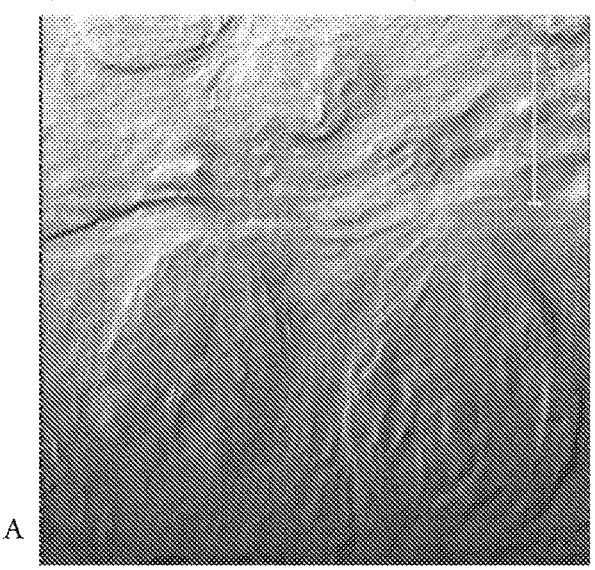
Figure 9D:
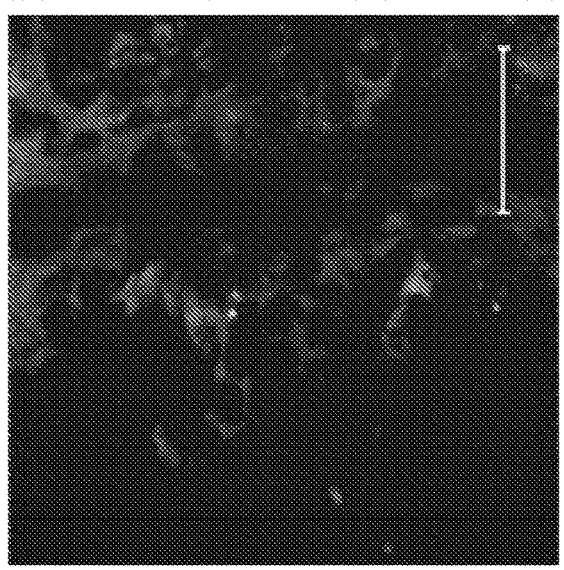
Figures 10A, 10B, 10C, 10D:
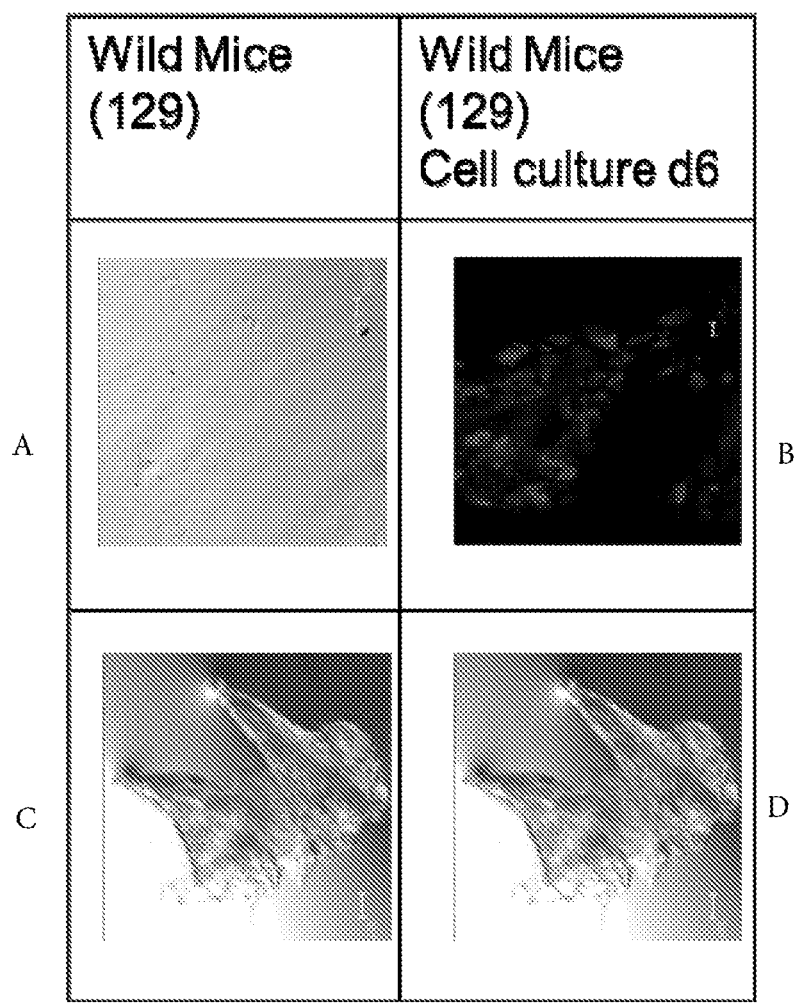
FIGS. 10A to 10D demonstrate that no signal induced by 488 nm wavelength (which induces GFP related signal) was observed in cultured wild mouse taste (M129) cells used to generate M71 and Eugenol transgenic mice. Freshly isolated taste tissue (FIGS. 10A and 10C) did not show any GFP expression after induced by 488 nm wavelength light. Cultured taste papillae cells (FIGS. 10B and 10D) obtained from M129 mice did not show any GFP expression when induced by 488 nm wavelength light. DAPI staining indicates nuclei of cells.
Figures 11A, 11B, 11C:
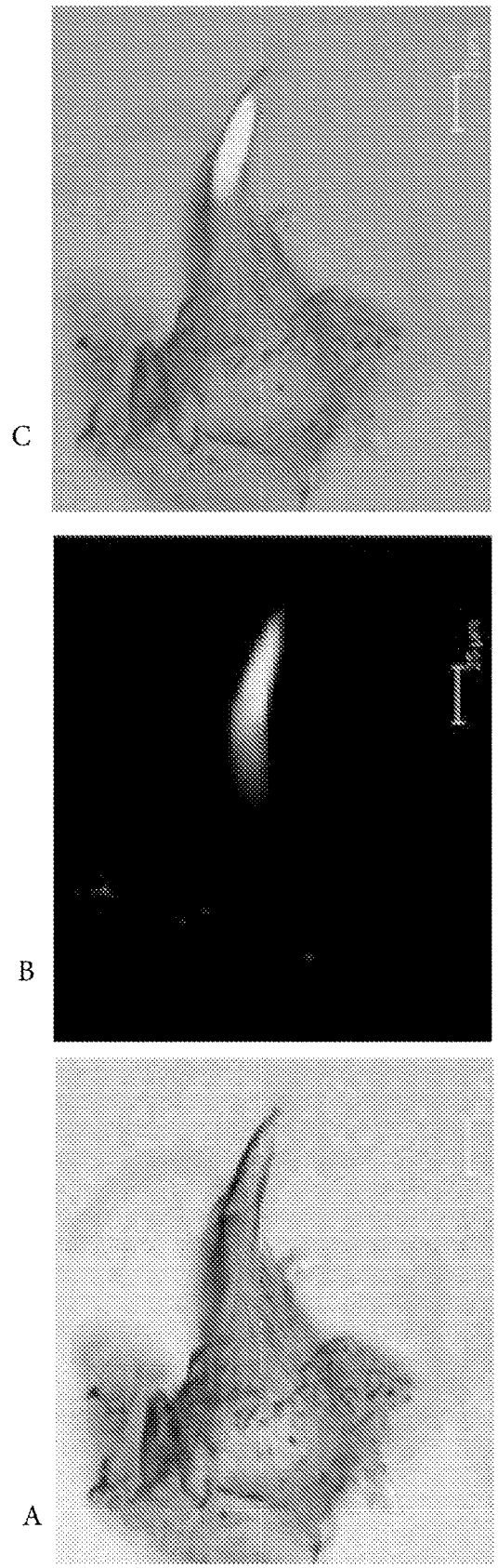
FIGS. 11A to 11C illustrate that freshly isolated taste tissue from mOR-M71-GFP ("M71") mice express GFP when induced by 488 nm wavelength light.

Expression of GFP Under Promoter of Olfactory Receptor in Taste Papillae Tissue of Genetically Modified Mice This study demonstrated the expression of physiologically active olfactory receptors on human and mice taste papillae cells. Taste papillae tissue obtained from mice genetically modified to express GFP under the control of the M71, I7 or Eugenol (EG) promoter were examined under confocal microscopy. GFP was expressed in taste papillae of the transgenic mice indicating the presence of I7, M71 and eugenol receptors in taste papillae cells. The expression of GFP was found localized specifically in taste papillae. As shown in FIGS. 1A-1D, mOR-I7-GFP transgenic mice demonstrated expression of green fluorescent protein in circumvallate taste papillae. As shown in FIGS. 2A-2C, mOR-M71-GFP transgenic mice demonstrated expression of green fluorescent protein in circumvallate taste papillae. mOR-EG-GFP transgenic mice demonstrated expression of GFP in circumvallate taste papillae (FIGS. 3A-3C and 4A-4B).

When taste tissue was stained with type II taste cell marker (PLC-b2 and gustducin), co-localization of GFP and PLC-b2 and gustducin expression in taste papillae cells was observed. PLC-b2 expression was demonstrated to co-localize with GFP expression in the circumvallate papillae of mOR-I7-GFP mice (FIGS. 5A-5D), mOR-M71-GFP transgenic mice (FIGS. 6A-6D), and mOR-EG-GFP transgenic mice (FIGS. 7A-7D). Gustducin expression also co-localized with GFP expression in circumvallate papillae of the mOR-M71-GFP transgenic mice (FIGS. 8A-8D) and mOR-EG-GFP transgenic mice (FIGS. 9A-9D).

In control experiments, no artefact signal of GFP from wild mouse (m129)—which does not have any GFP expression vector—was observed (FIGS. 10A-10D). Freshly isolated m129 taste cells also did not express GFP, while freshly isolated taste tissue from mOR-M71-GFP mice did express GFP (FIGS. 11A-11D). Interestingly, mouse filiform papillae expressed GFP protein indicating possible presence of olfactory receptors in non-taste cells of tongue.

Figures 12A, 12B, 12C, 12D, 12E, 12F:
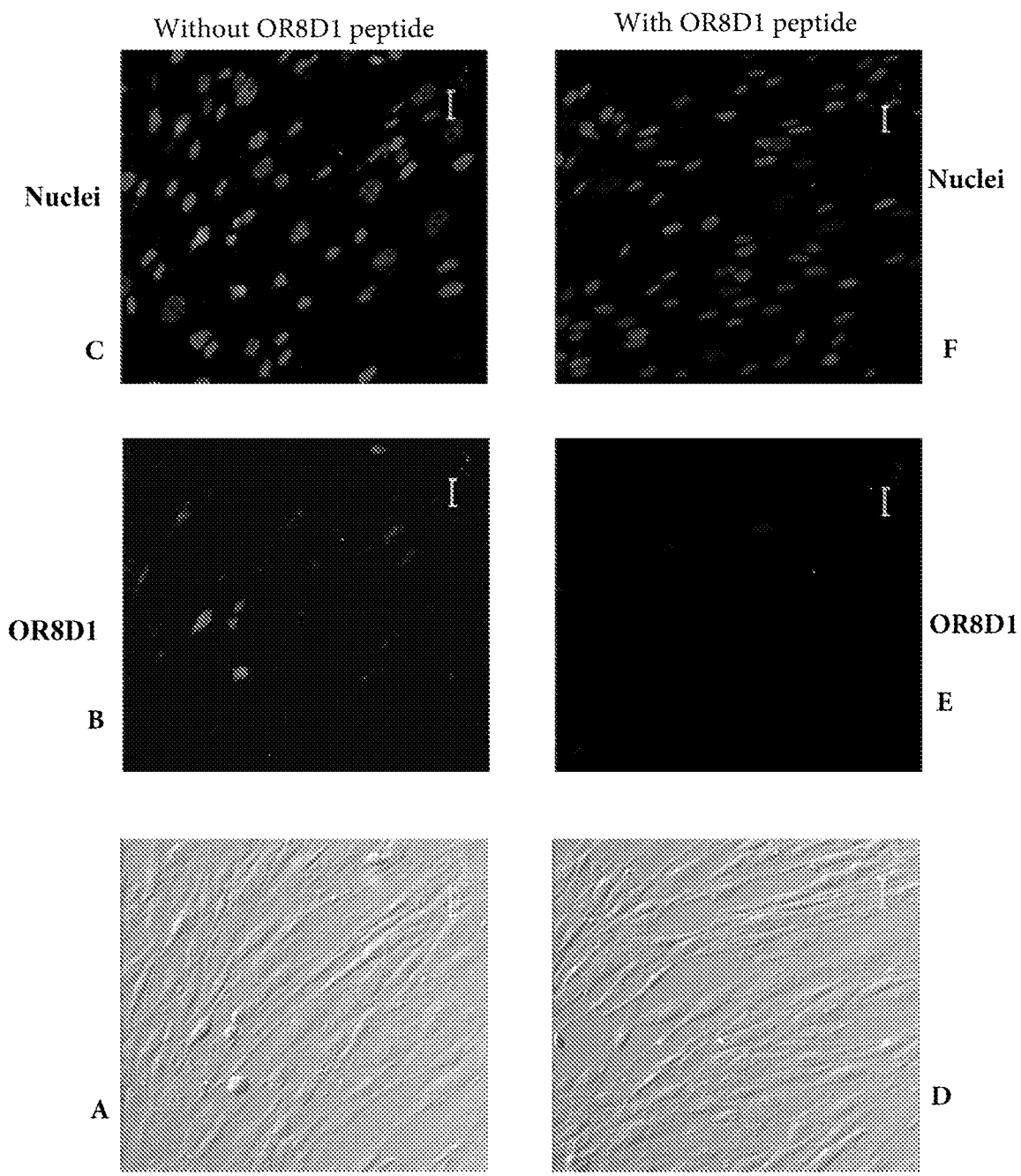
FIGS. 12A to 12F illustrate the expression of OR8D1 in cultured human fungiform taste cells as confirmed by a peptide inhibition assay.

In addition to mouse tissue, the presence of olfactory receptors was examined in cultured human fungiform taste papillae cells (HBO). Cultured human fungiform taste papillae (HBO) cells were stained with OR8D1 receptor antibody (SantaCruz) indicating expression of OR8D1 protein (FIGS. 12A-12C). Specificity of OR8D1 was examined by utilizing peptide inhibition assay. Specifically, OR8D1 antibody was pre-incubated with its own specific peptide to determine the specificity of OR8D1 immunoreactivity. OR8D1 antibody incubated with its specific peptide resulted in complete removal of OR8D1 specific immunoreactivity (FIGS. 12D-12F).

EXAMPLE 4

Olfactory Properties of Mammalian Taste Cells

Figure 13:
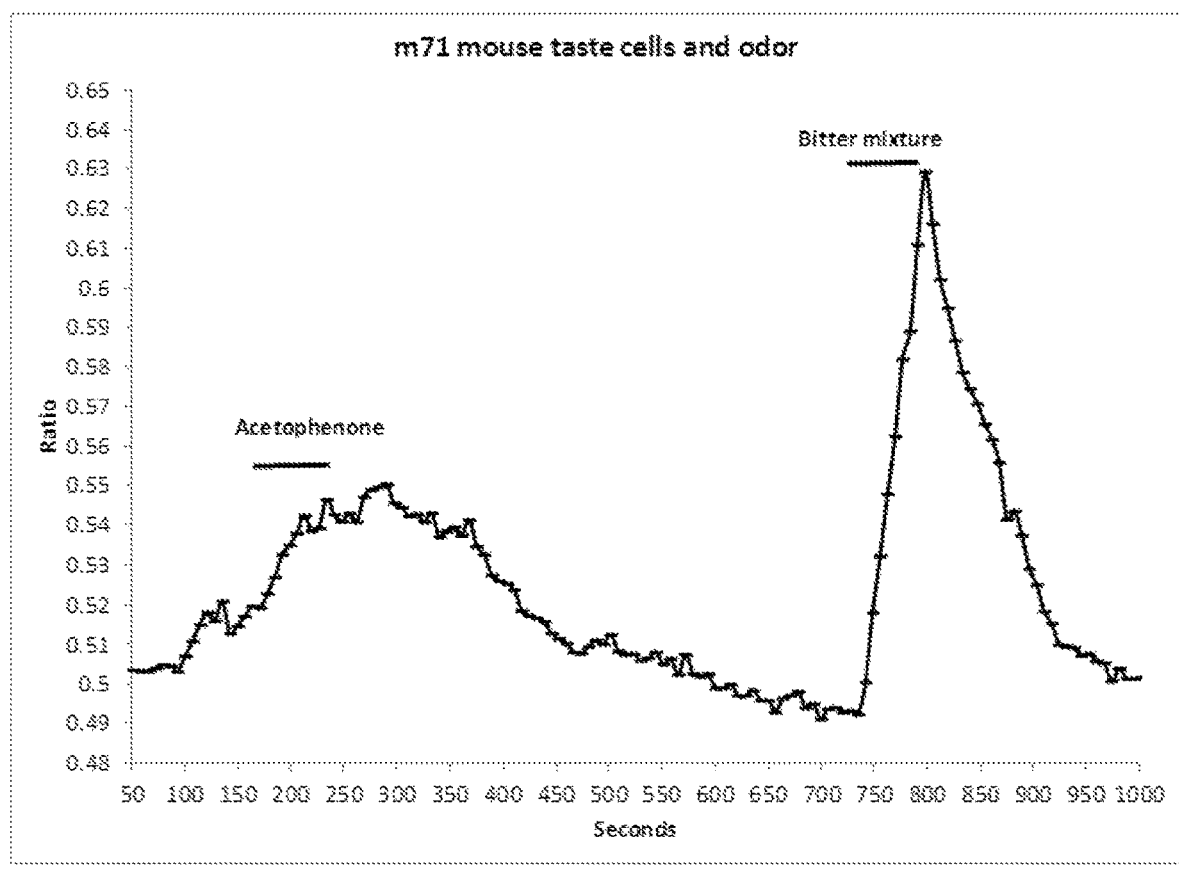
FIG. 13 is a graph that demonstrates that cultured taste papillae cells obtained from mOR-M71-GFP ("M71") mice respond to receptor specific odor, acetophenone and bitter mixture, indicating both olfactory and taste receptors on single cells.
Figure 14:
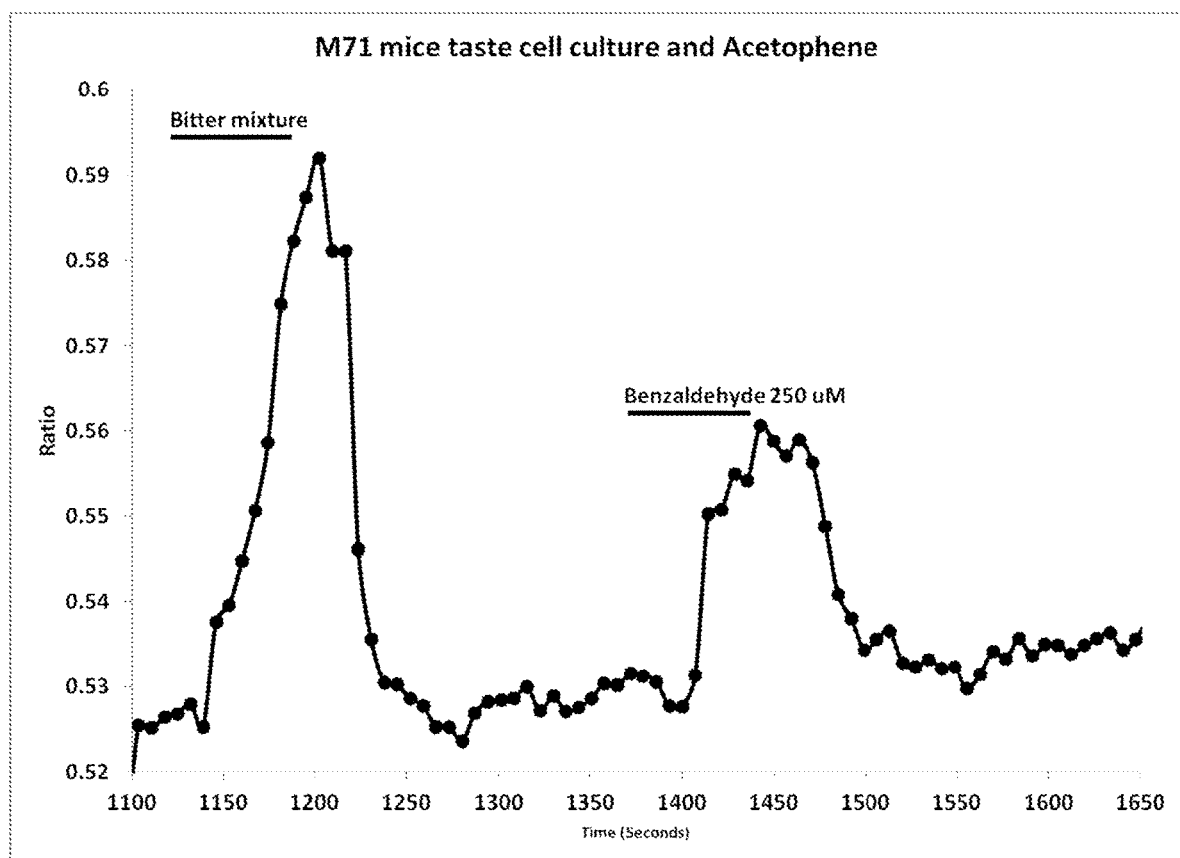
FIG. 14 demonstrates that cultured taste papillae cells obtained from mOR-M71-GFP ("M71") mice respond to receptor specific odor, benzaldehyde and bitter mixture, indicating both taste and olfactory receptors on single cells.
Figure 15:
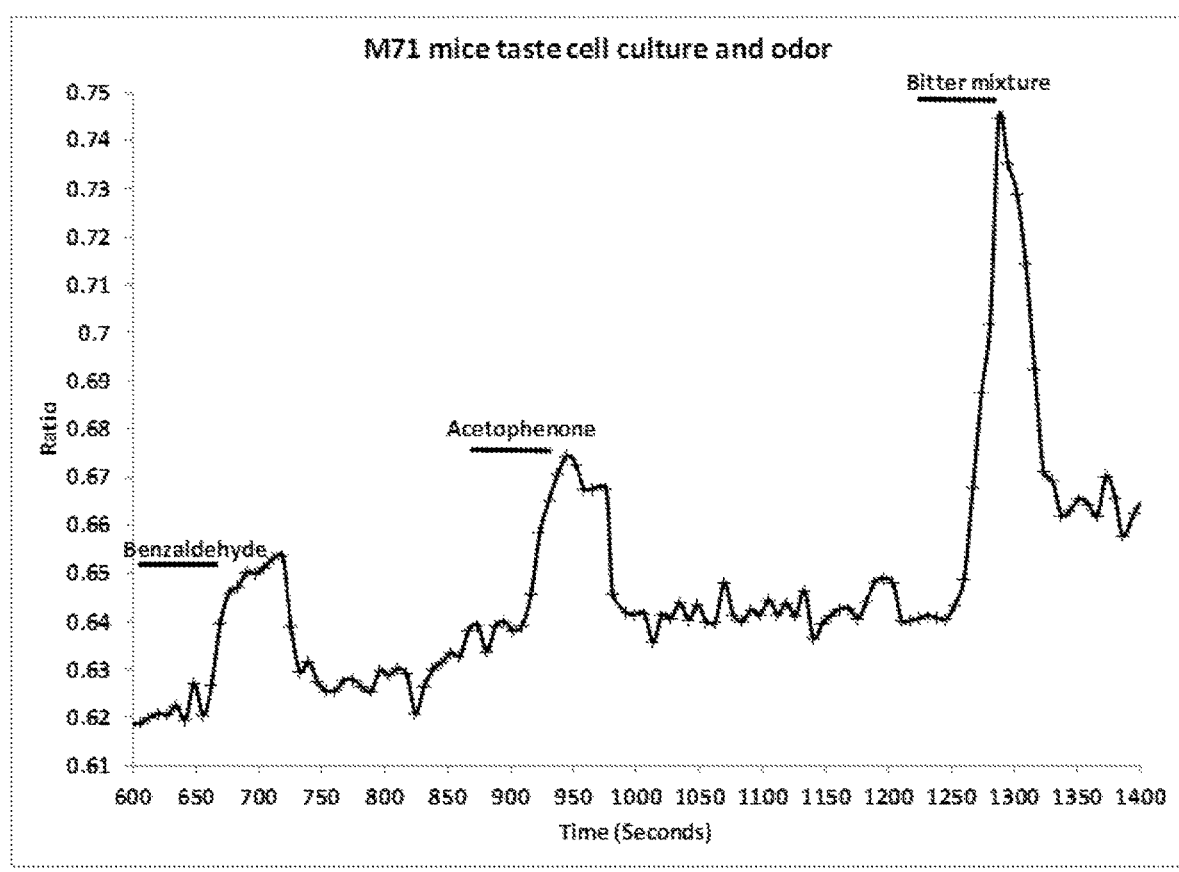
FIG. 15 demonstrates that cultured taste papillae cells obtained from mOR-M71-GFP ("M71") mice respond to receptor specific odors, acetophenone and benzaldehyde and bitter mixture, indicating both olfactory and taste receptors on single cells.

Affymetrix RNA analysis of cultured human fungiform taste papillae demonstrated the presence of more than 400 olfactory receptor related mRNAs. The functional olfactorial characteristics of mammalian taste cells also were examined Specifically, olfactorial characteristics of cultured wild (m129), M71 and Eugenol mice taste cells as well as cultured human fungiform taste papillae cells were examined by calcium imaging with different odors specific to certain olfactory receptors. It was found that cultured taste papillae cells from wild (m129) and transgenic mice as well as from human demonstrate strong response to receptor-specific odorants at optimal concentration (100 uM) indicating presence of odor specific receptors in mammalian taste cells. It was further demonstrated that odorant responsive cultured taste cells respond to bitter mixture. In particular, mOR-M71-GFP mouse taste cell cultures (between day 2 to day 6) exhibited a response to acetophenone (not shown) and to acetophenone and bitter mixture (FIG. 13). Cultured taste papillae cells obtained from mOR-M71-GFP mice responded to receptor specific odor, benzaldehyde, and bitter mixture (FIG. 14). Cultured taste papillae cells obtained from mOR-M71-GFP mice responded to receptor specific odors, acetophenone and benzaldehyde and bitter mixture (FIG. 15).

Figure 16:
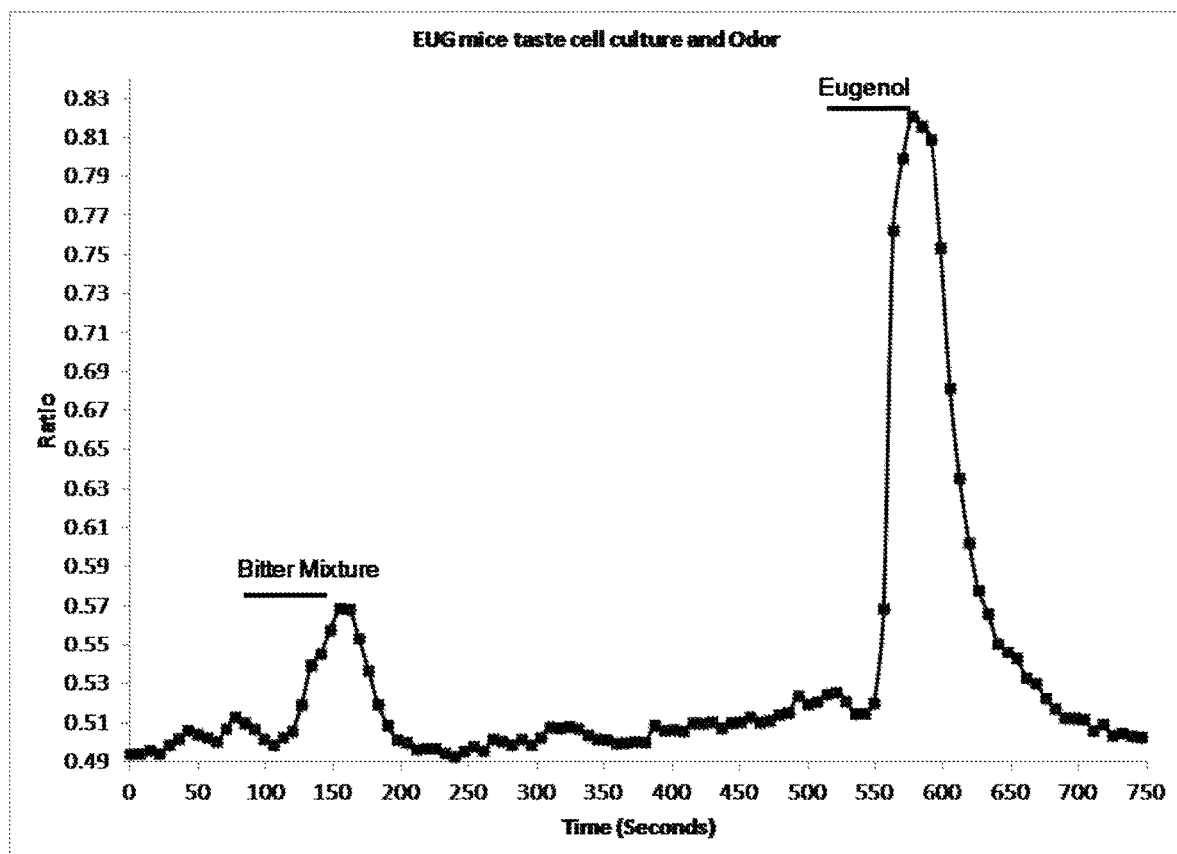
FIG. 16 demonstrates that cultured taste papillae cells obtained from mOR-EG-GFP ("mEUG") mice respond to receptor specific odor, eugenol and bitter mixture, indicating both taste and olfactory receptors on single cells. Cultured taste papillae cells obtained from mOR-EG-GFP mice specifically indicate both olfactory and taste receptors on single cells.
Figure 17:
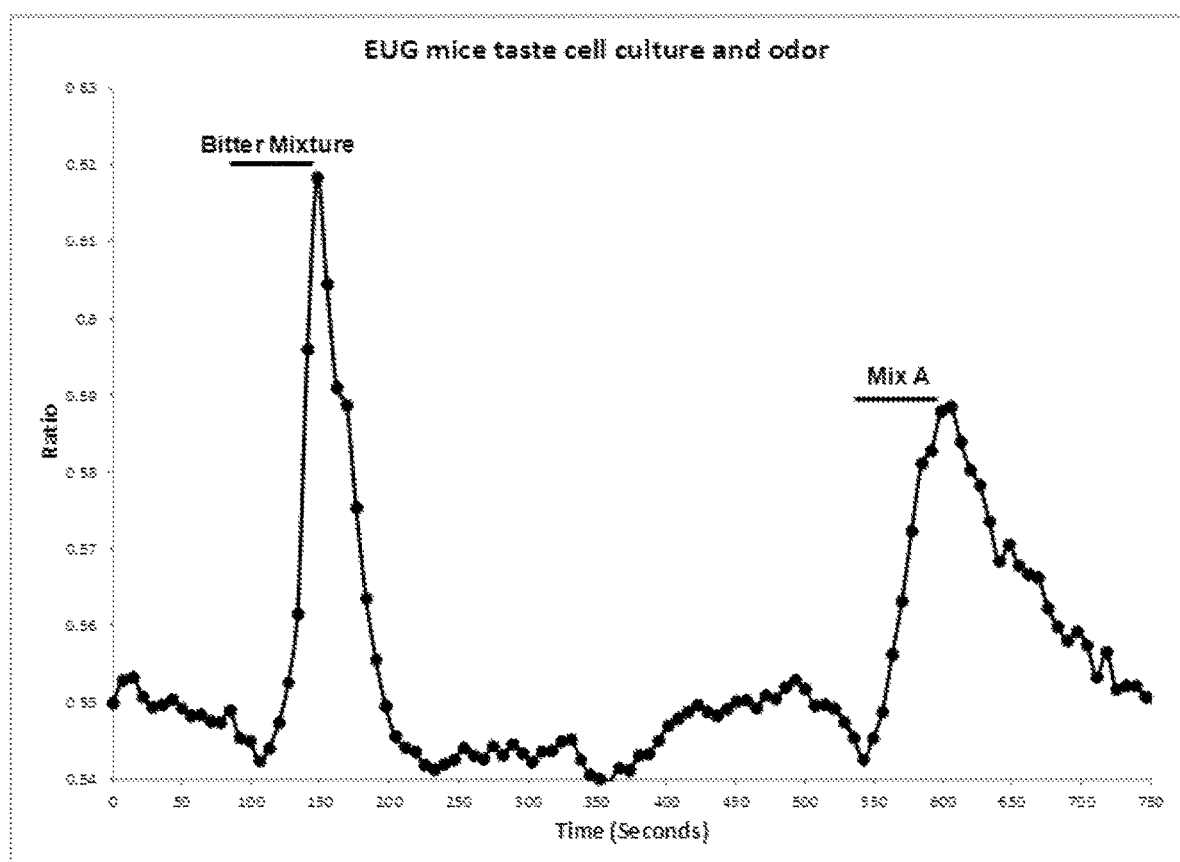
FIG. 17 demonstrates that cultured taste papillae cells obtained from mOR-EG-GFP ("mEUG") mice respond to bitter mixture and Mix A, indicating both taste and olfactory receptors on single cells.
Figure 18:
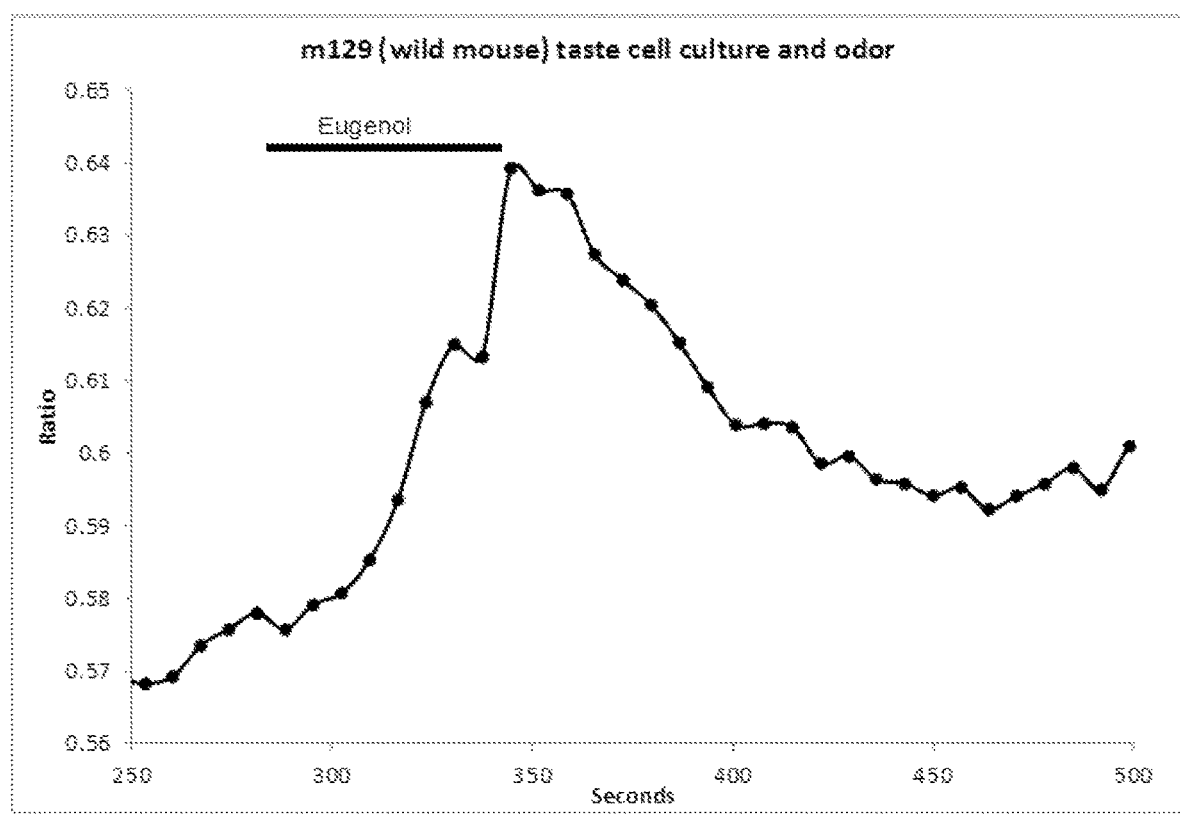
FIG. 18 demonstrates that cultured taste papillae cells obtained from M129 mice are sensitive to eugenol.
Figure 19:
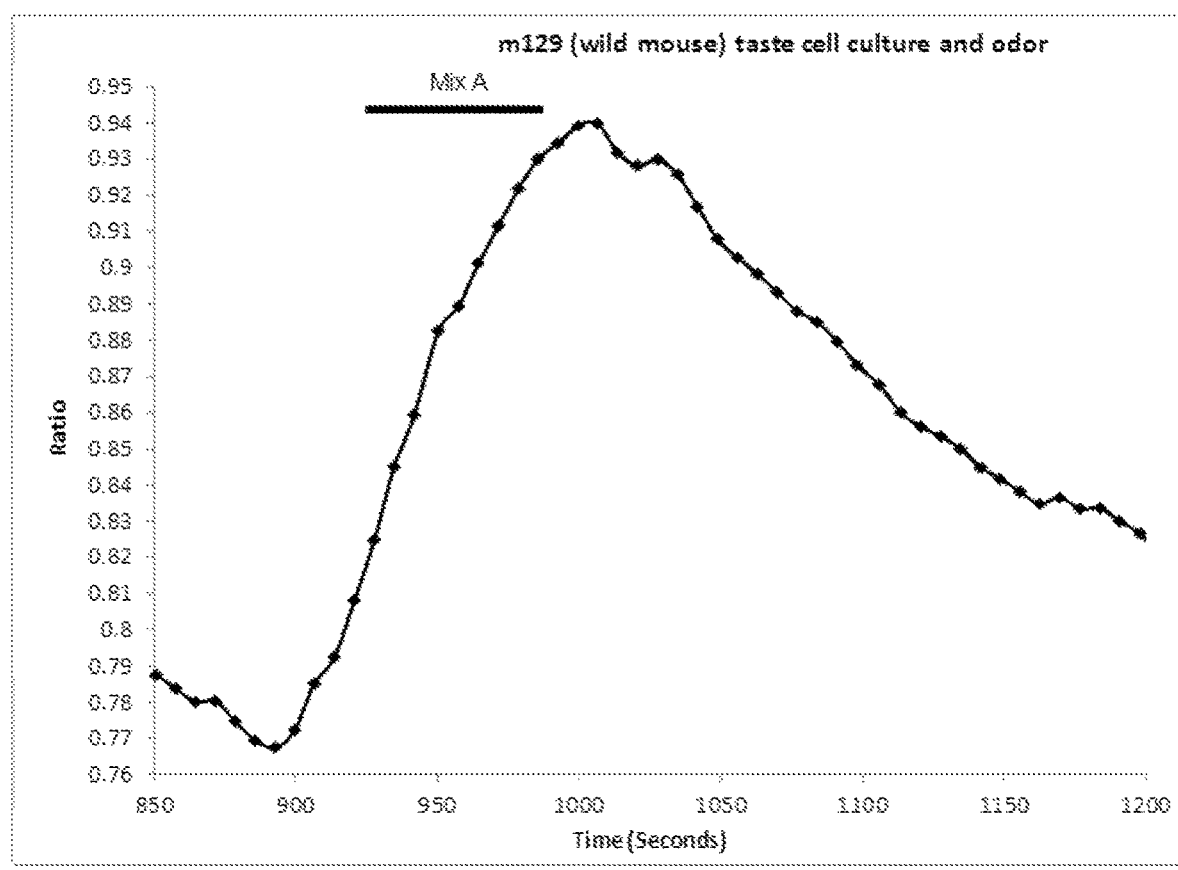
FIG. 19 demonstrates that cultured taste papillae cells obtained from M129 mice are sensitive to Mix A.
Figure 20:
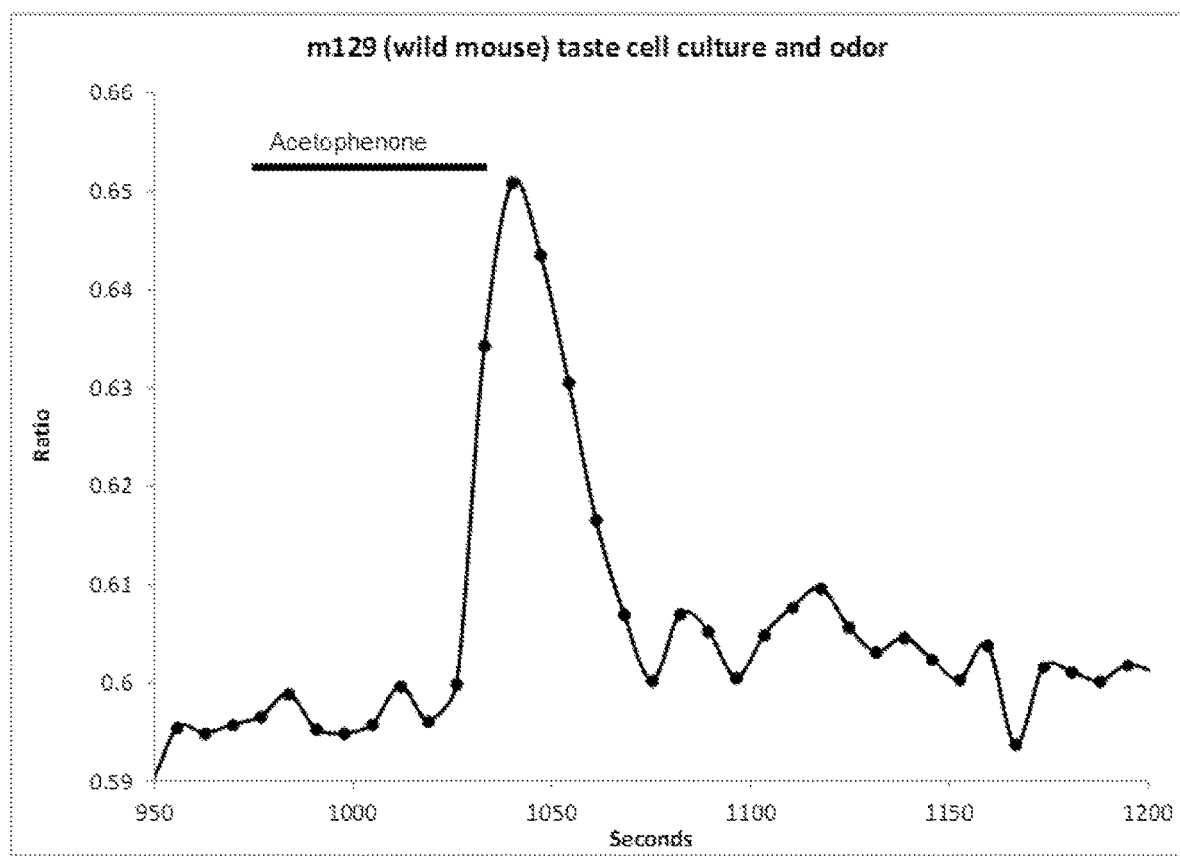
FIG. 20 demonstrates that cultured taste papillae cells obtained from M129 mice are sensitive to acetophenone.
Figure 21:
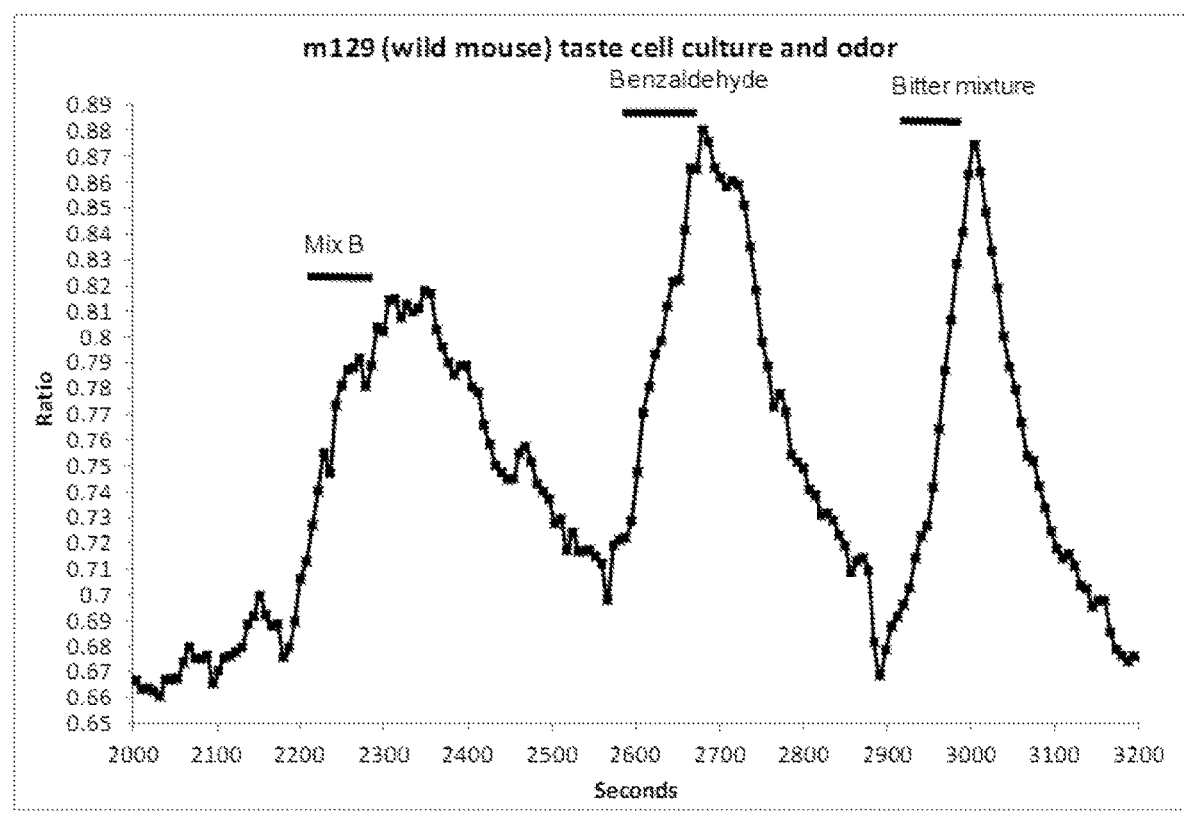
FIG. 21 demonstrates that cultured taste papillae cells obtained from M129 mice are sensitive to Mix B, benzaldehyde, and bitter mixture, indicating both taste and olfactory receptor on single cells.

In addition, cultured taste papillae cells obtained from mOR-EG-GFP mice responded to receptor specific odor, eugenol (FIG. 16). Cultured (day 4) mouse taste cells obtained from mOR-EG-GFP mice responded to bitter mix and Mix A (not shown). Cultured taste papillae cells obtained mOR-EG-GFP mice responded to bitter mixture and Mix A (FIG. 17). Cultured wild mouse (m129) taste papillae cells responded to benzaldehyde (FIG. 21), mix A (FIG. 19), acetophenone (FIG. 20), and mix B (FIG. 21).

Figure 22:
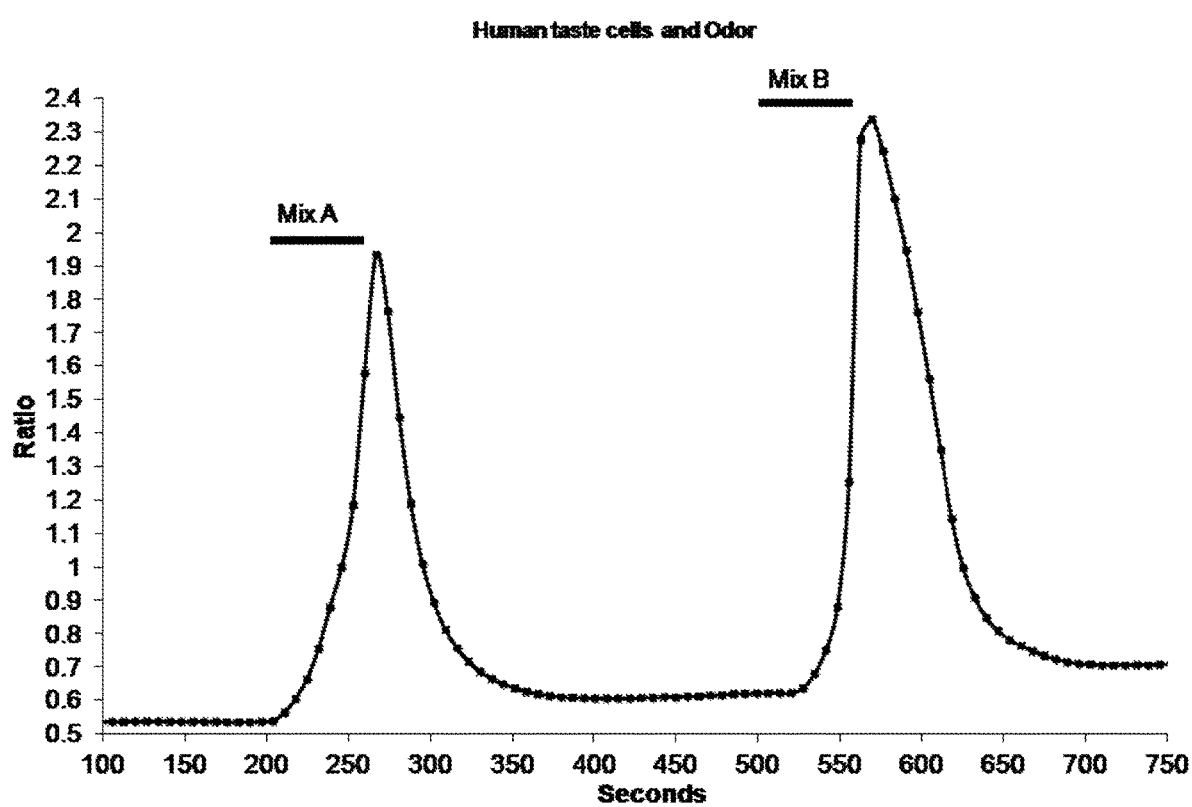
FIG. 22 demonstrates that cultured fungiform taste papillae (HBO) cells obtained from human tongue responded to odor stimuli Mix A and Mix B. Changes in intracellular calcium levels ([Ca2+]i) in cultured human fungiform taste cell were measured using fura-2 standard calcium imaging system. Graphs illustrate representative changes in [Ca+2]i levels in individual cells during exposure to odor. Stimuli were dissolved in ringer solution and adjusted for pH and osmolarity.

It was found that cultured human fungiform taste papillae cells demonstrated response to specific odorants at optimal concentration (100 uM) indicating presence of odor specific receptors in mammalian taste cells. It was also demonstrated that odorant responsive cultured taste cells respond to bitter mixture. To confirm the relation between odor responsive cells and bitter responsive cells, cells were fixed after calcium imaging. Cultured fungiform taste papillae (HBO) cells obtained from human tongue are sensitive to Mix A and Mix B (FIG. 22). Cultured human taste cells responded to odor stimuli. Changes in intracellular calcium levels ([Ca2+]i) in cultured human fungiform taste cell were measured using fura-2 standard calcium imaging system. Stimuli were dissolved in ringer solution and adjusted for pH and osmolarity. Graphs illustrate representative changes in [Ca+2]i levels in individual cells during exposure to odor.

Figure 23:
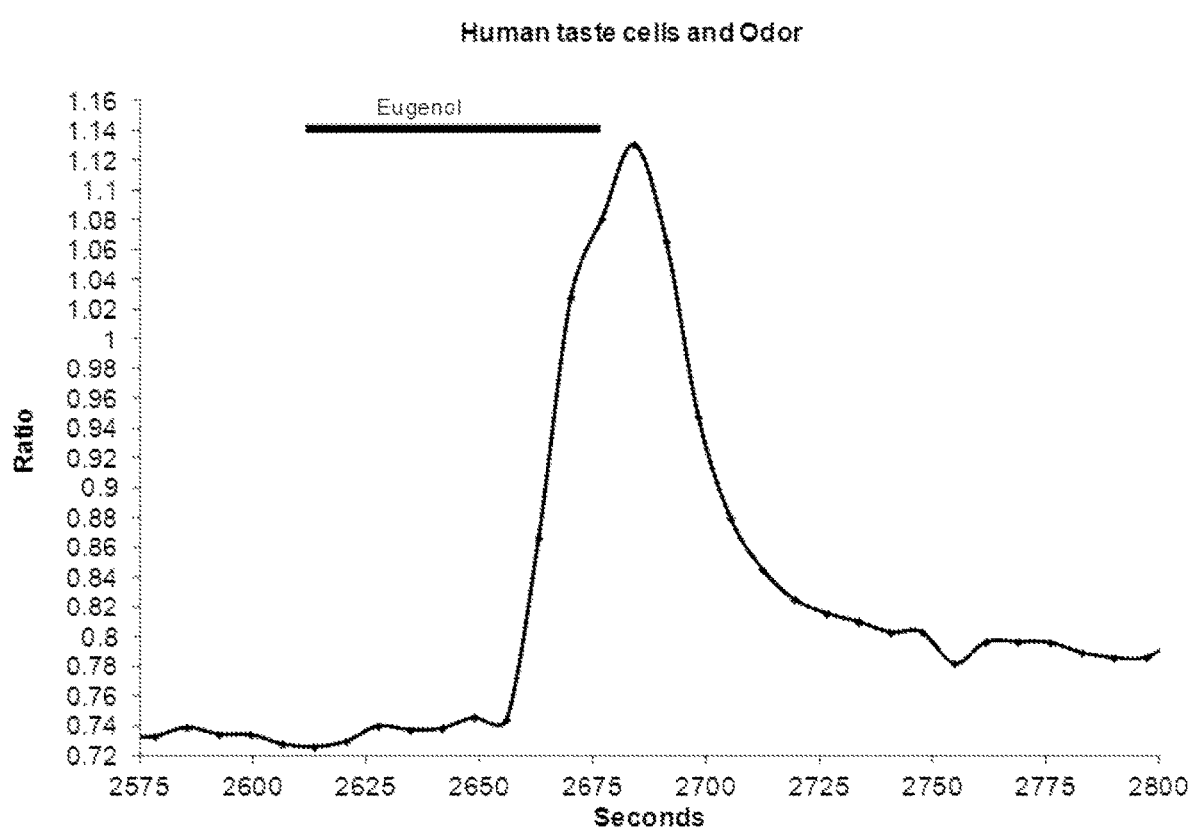
FIG. 23 demonstrates that cultured fungiform taste papillae (HBO) cells obtained from human tongue are sensitive to Eugenol. Possible receptor involved in the response is human OR5D18 (or mouse Olfr73).
Figure 24:
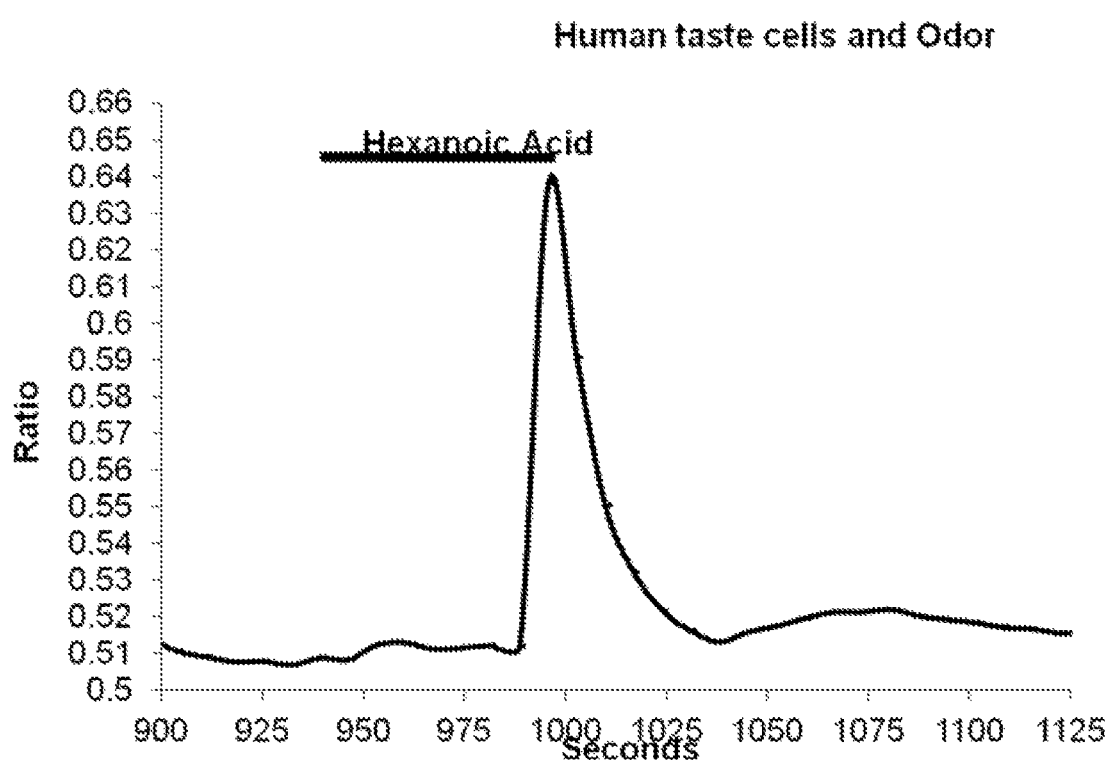
FIG. 24 demonstrates that cultured fungiform taste papillae (HBO) cells obtained from human tongue are sensitive to hexanoic acid. Possible receptor involved in the response is human OR51L1 (or mouse Olfr64 and/or Olfr653).
Figure 25:
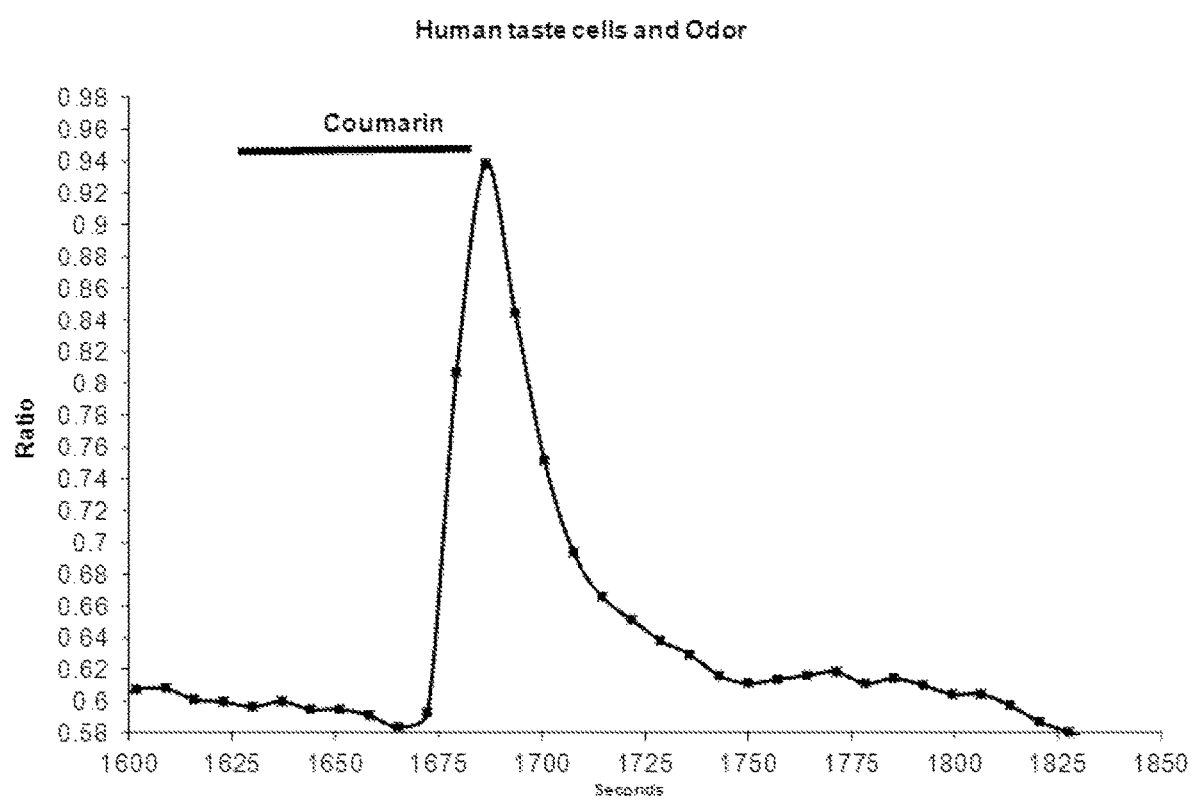
FIG. 25 demonstrates that cultured fungiform taste papillae (HBO) cells obtained from human tongue are sensitive to coumarin. Receptors involved in the response are likely one or more of human OR2J2, OR2W1, and OR5P3 (or mouse Olfr1519, Olfr749, Olfr1352, Olfr1079, Olfr1377, Olfr556, Olfr1341, Olfr1062, Olfr109, Olfr508, Olfr983, Olfr876, Olfr1104, and Olfr895).

Cultured HBO cells obtained from human tongue are sensitive to eugenol (FIG. 23). Possible receptor involved in the response is human OR5D18 (or mouse Olfr73). Cultured HBO cells obtained from human tongue are sensitive to hexanoic acid (FIG. 24). One possible receptor involved in the response is human human OR51L1 (or mouse Olfr64 and/or Olfr653). Cultured HBO cells obtained from human tongue also are sensitive to coumarin (FIG. 25). Possible receptors involved in the response are human OR2J2, OR2W1, and OR5P3 (or mouse Olfr1519, Olfr749, Olfr1352, Olfr1079, Olfr1377, Olfr556, Olfr1341, Olfr1062, Olfr109, Olfr508, Olfr983, Olfr876, Olfr1104, and Olfr895).

Figure 26:
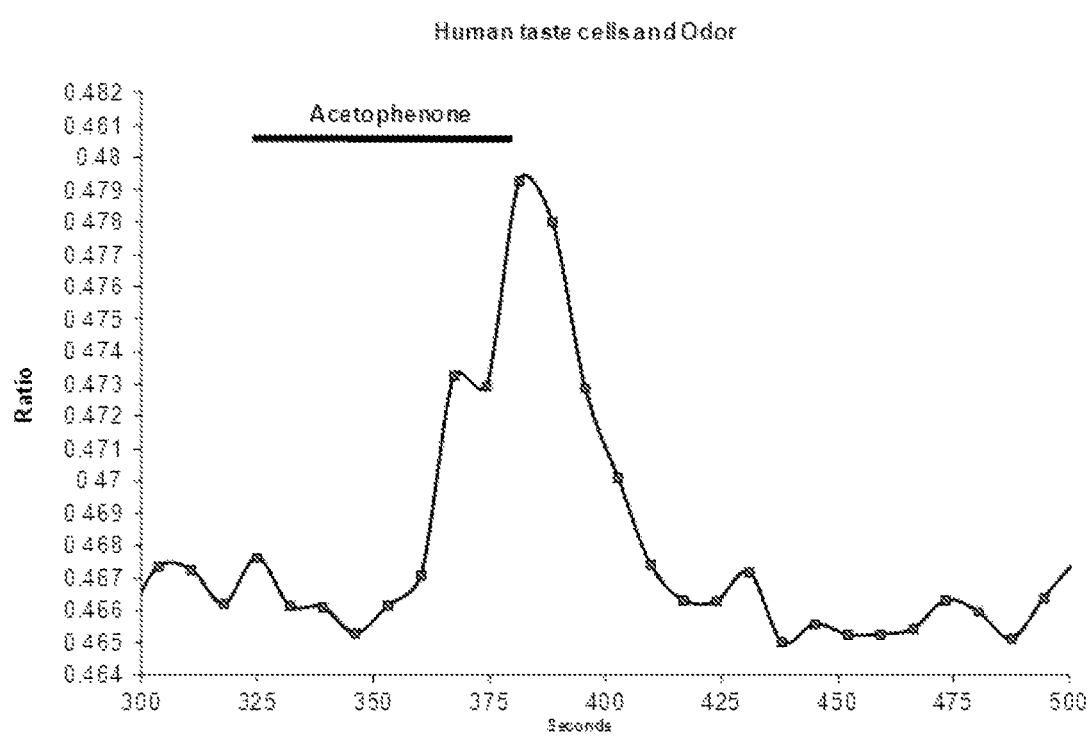
FIG. 26 demonstrates that cultured fungiform taste papillae (HBO) cells obtained from human tongue are sensitive to acetophenone. Receptors involved in the response are one or more of human OR2W1 and OR5P3 (or mouse Olfr749, Olfr1352, Olfr1079, Olfr1377, Olfr556, Olfr1341, Olfr1062, Olfr109, Olfr983, Olfr876, Olfr1104, Olfr895, Olfr168, Olfr429, Olfr167, and Olfr151).
Figure 27:
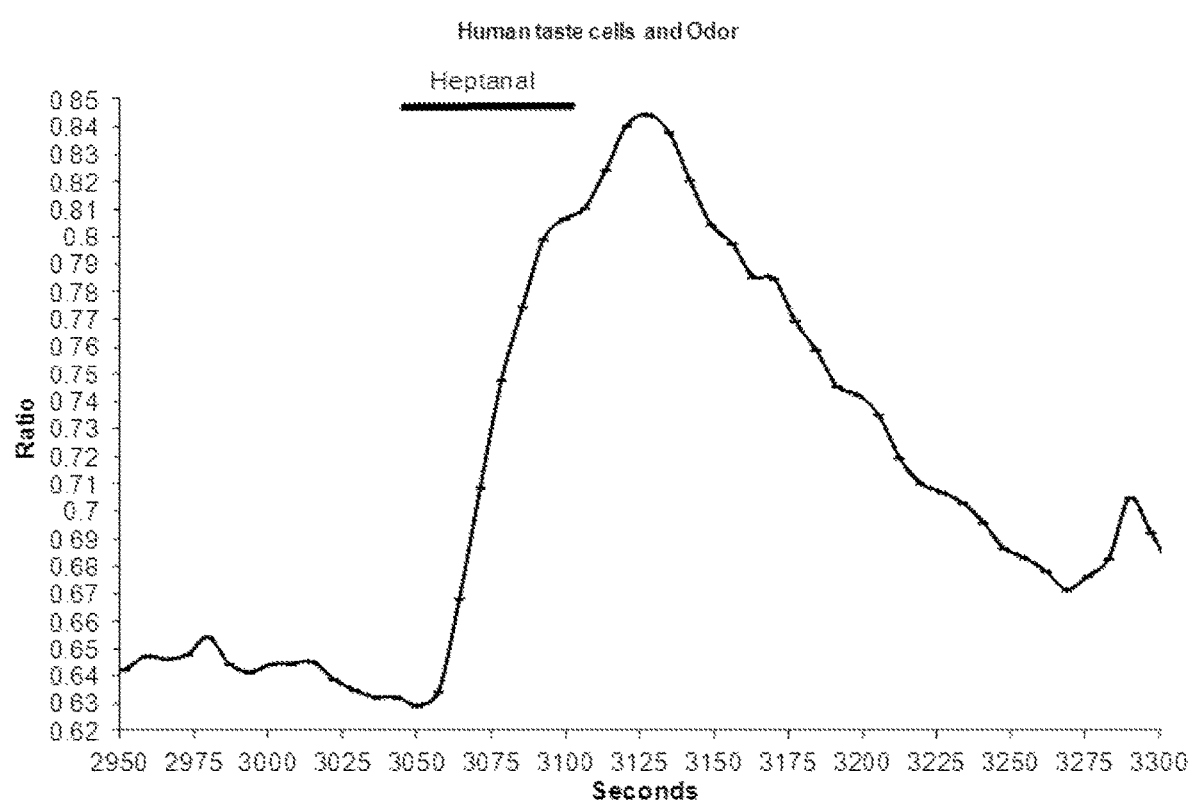
FIG. 27 demonstrates that cultured fungiform taste papillae (HBO) cells obtained from human tongue are sensitive to heptanal. Receptor involved in the response is likely OR2W1 (or mouse Olfr17).
Figure 28:
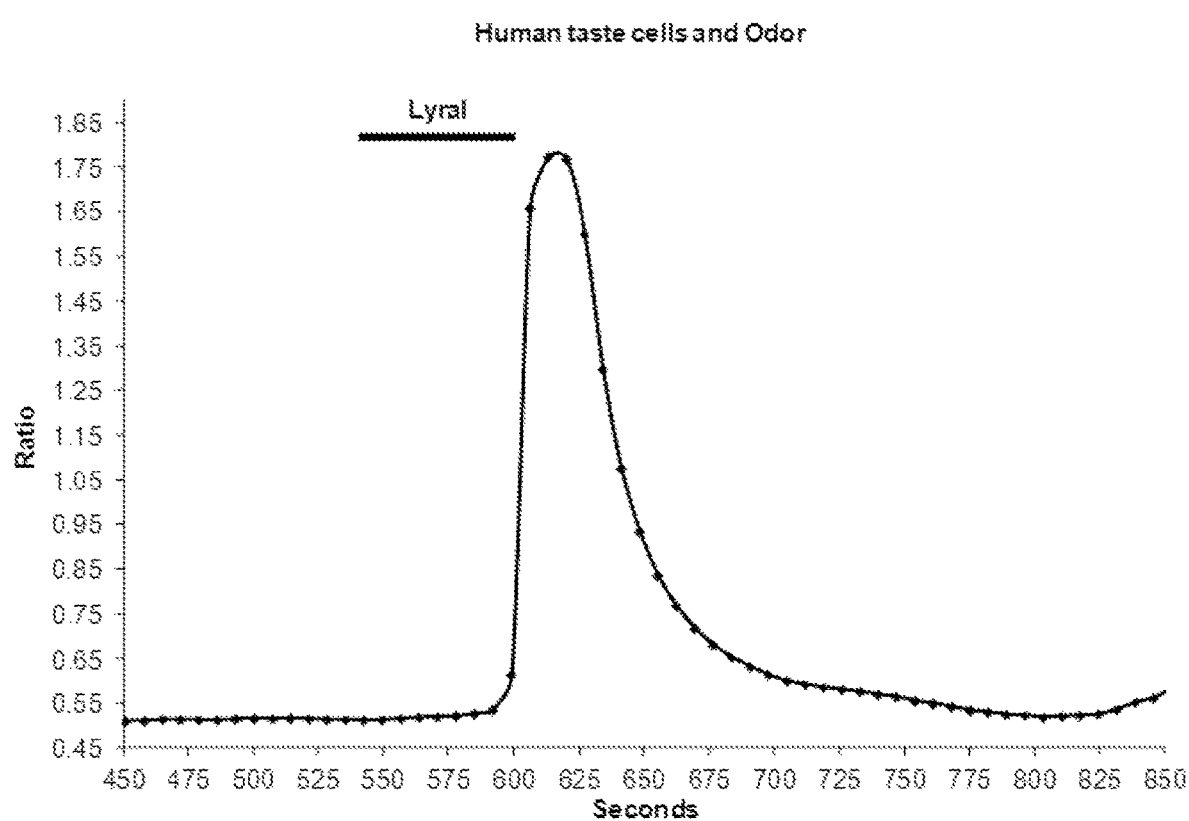
FIG. 28 demonstrates that cultured fungiform taste papillae (HBO) cells obtained from human tongue are sensitive to lyral. Receptor involved in the response is human OR10J5 (or mouse Olfr15 and Olfr16).

Cultured HBO cells obtained from human tongue are sensitive to acetophenone (FIG. 26). Possible receptors involved in the response are human OR2W1 and OR5P3 (or mouse Olfr749, Olfr1352, Olfr1079, Olfr1377, Olfr556, Olfr1341, Olfr1062, Olfr109, Olfr983, Olfr876, Olfr1104, Olfr895, Olfr168, Olfr429, Olfr167, and Olfr151). Cultured HBO cells obtained from human tongue are sensitive to heptanal (FIG. 27). A possible receptor involved in the response is OR2W1 (or mouse Olfr17). Cultured HBO cells obtained from human tongue are sensitive to lyral (FIG. 28). One possible receptor involved in the response is human OR10J5 (or mouse Olfr15 and Olfr16).

EXAMPLE 5

The Relation Between Odor Responsive Cells and Bitter Responsive Cells

Figures 29A, 29B, 29C:
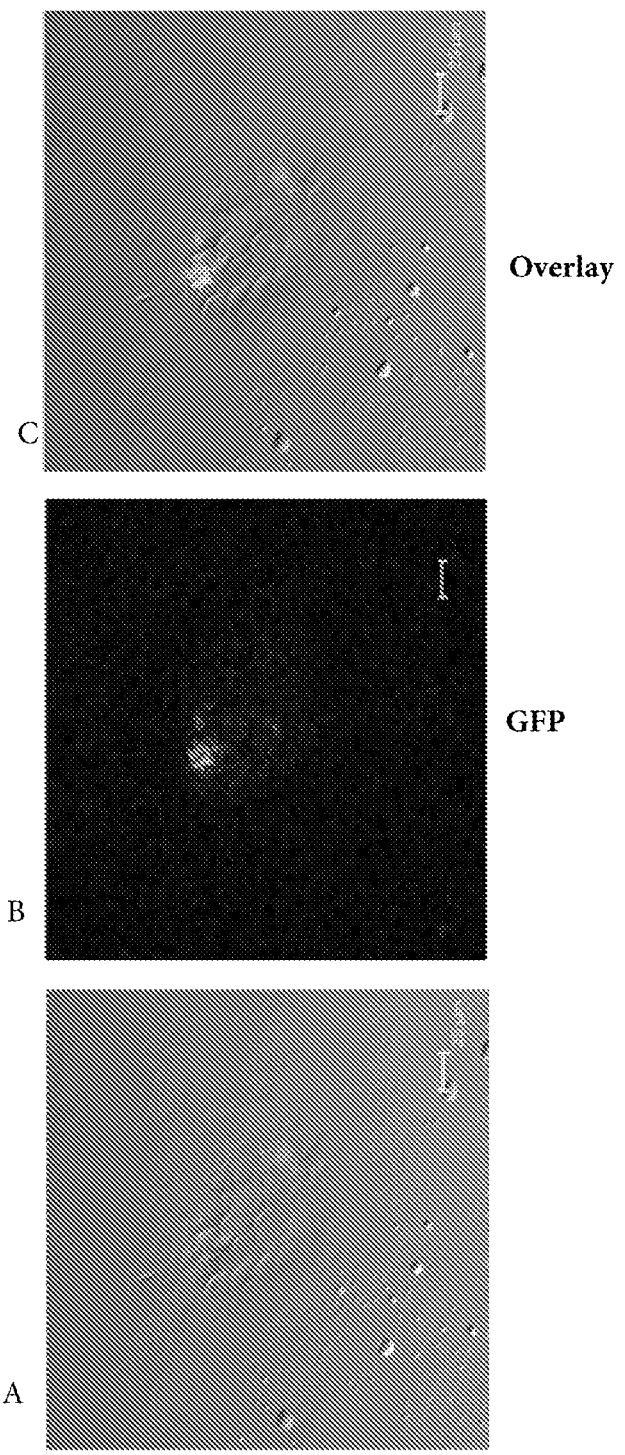
FIGS. 29A to 29C show the expression of GFP in cultured taste papillae cells obtained from mOR-EUG-GFP mice which was responsive to eugenol. Picture was taken after calcium imaging.
Figures 30A, 30B, 30C:
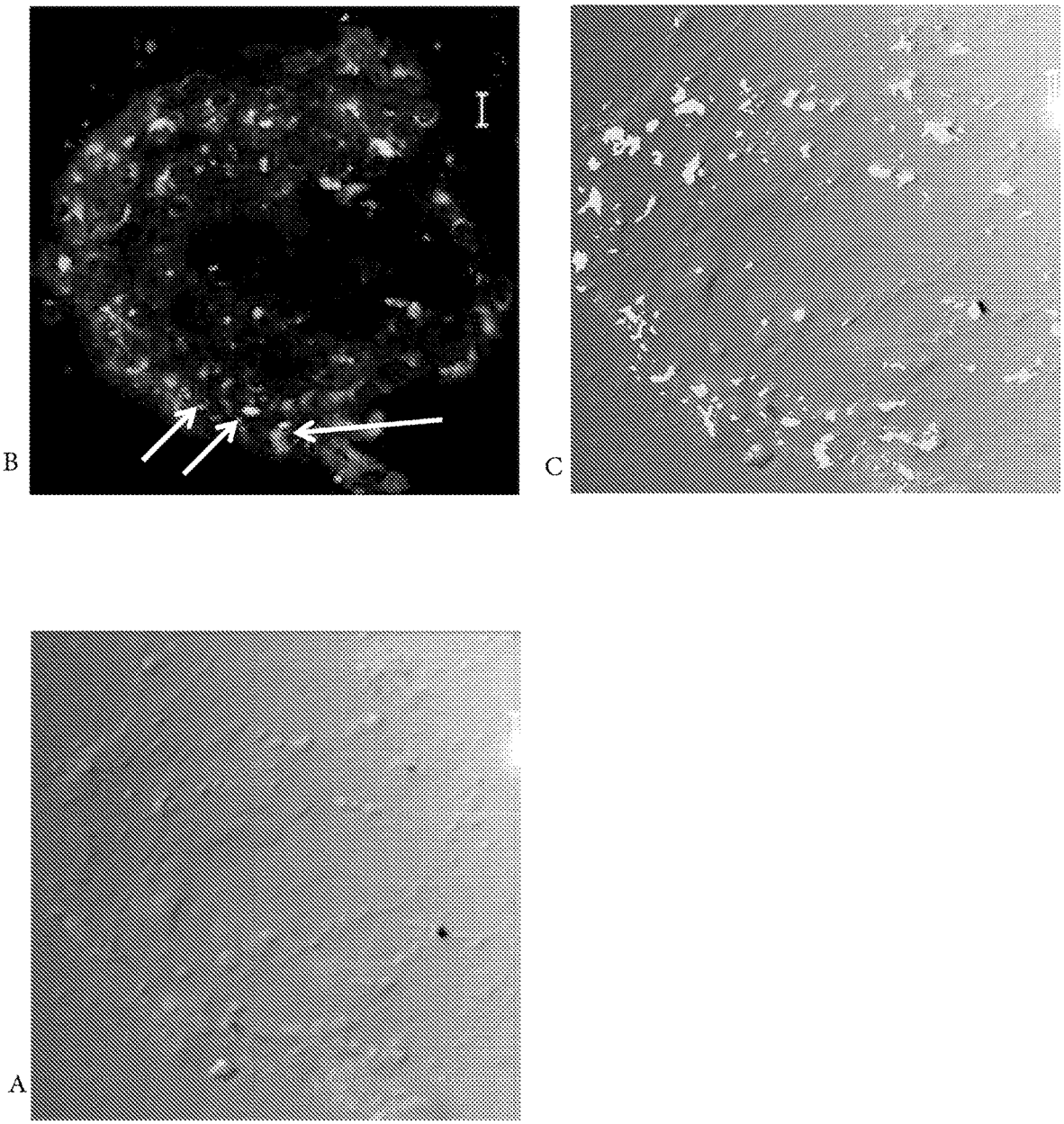
FIGS. 30A to 30C show the expression of GFP in cultured taste papillae cells obtained from mOR-M71-GFP mice which was responsive to acetophenone. This image was taken after calcium imaging. Responsive cells labeled with arrow demonstrated the expression of GFP.

Cultured taste cells obtained from mOR-EG-GFP transgenic mice were fixed after calcium imaging. The view used for calcium imaging and responsive cells was located. It was found that responsive cells express GFP indicating that odorant stimulates the cells to express their own receptors. It was also observed that odorant responsive and GFP-positive cells were also responsive to bitter stimuli. In particular, FIGS. 29A-29C show that mOR-EG-GFP cultured taste papillae cells respond to eugenol after calcium imaging. FIGS. 30A-30C show that mOR-M71-GFP cultured taste papillae cells respond to acetophenone after calcium imaging. The view used for calcium imaging and responsive cells was located. It was found that responsive cells express GFP indicating that odorant stimulates the cells to express their own receptors. It was also observed that odorant responsive and GFP-positive cells were also responsive to bitter stimuli.

EXAMPLE 6

Transient Expression of Odor Receptors in Cells

Figure 31A:
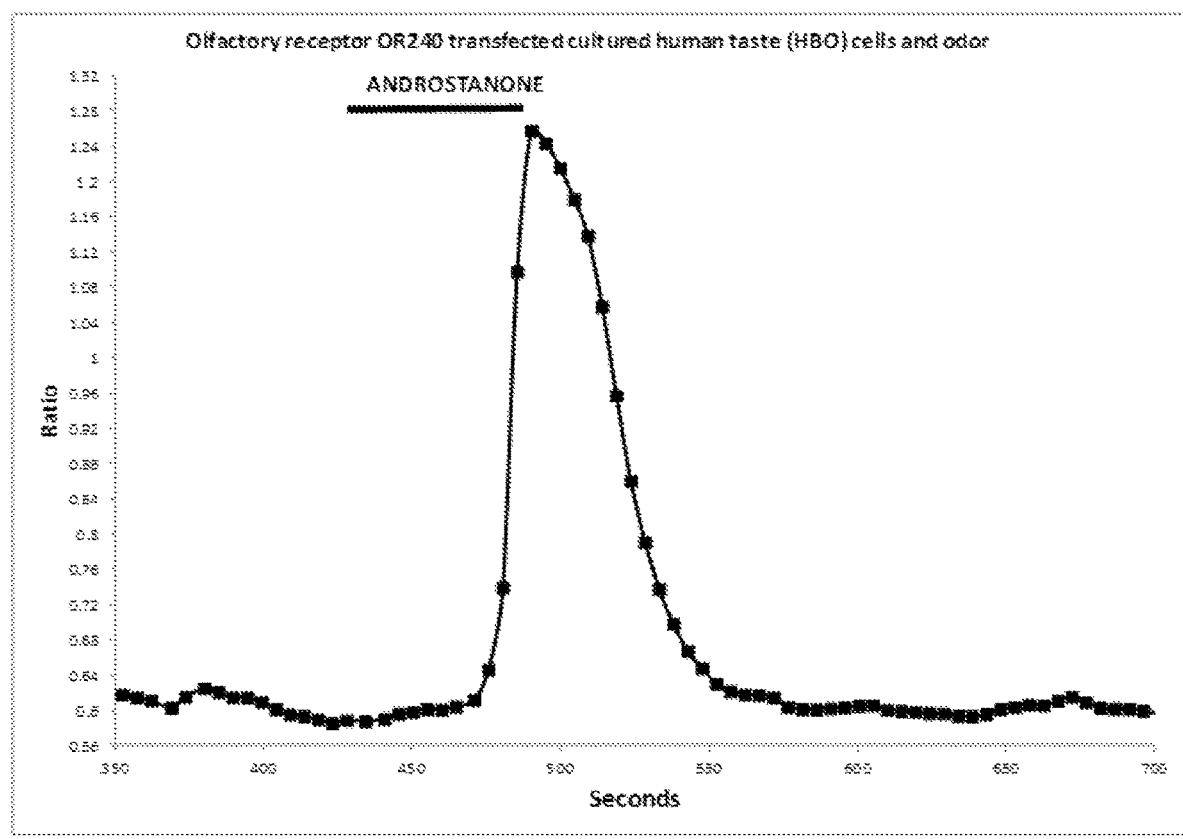
FIGS. 31A and 31B are graphs that demonstrate that cultured taste cells transfected with OR7D4 or OR5S6 display increased calcium response to odor ligands for the respective receptors.
Figure 31B:
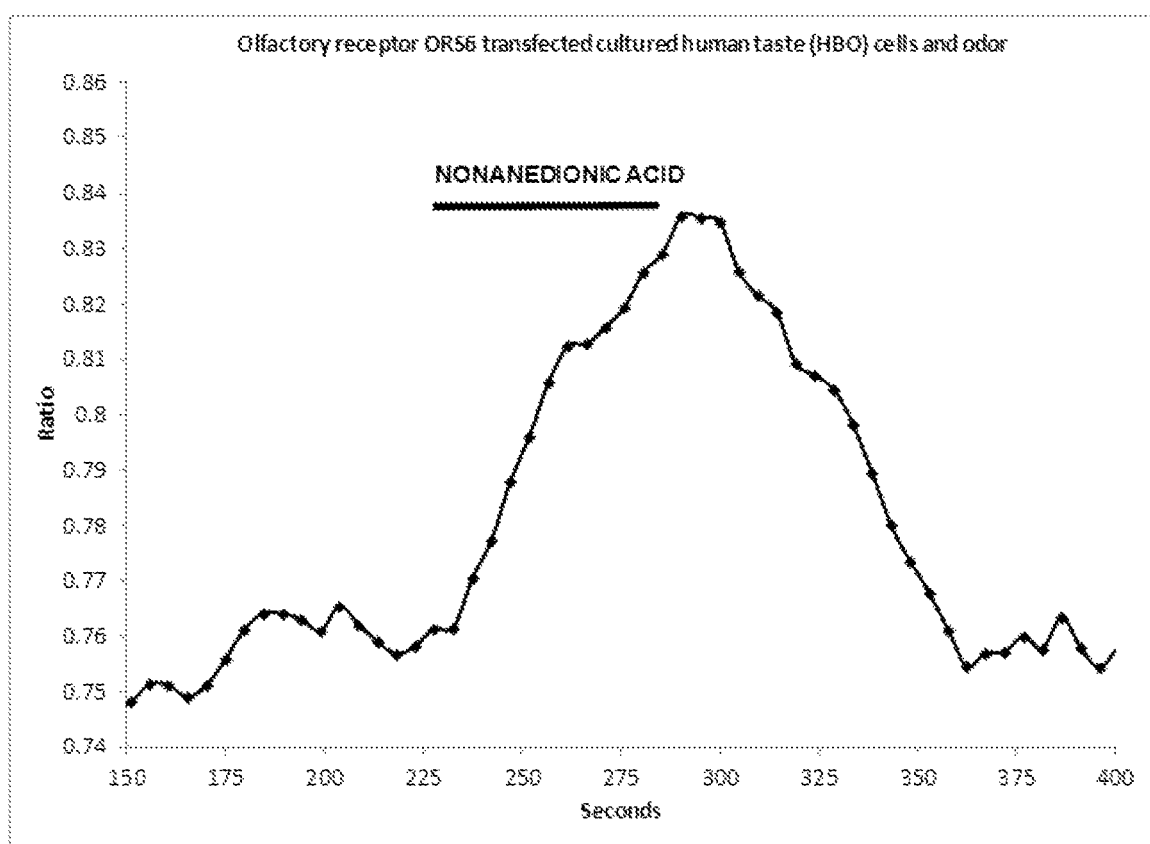
Figure 32A:
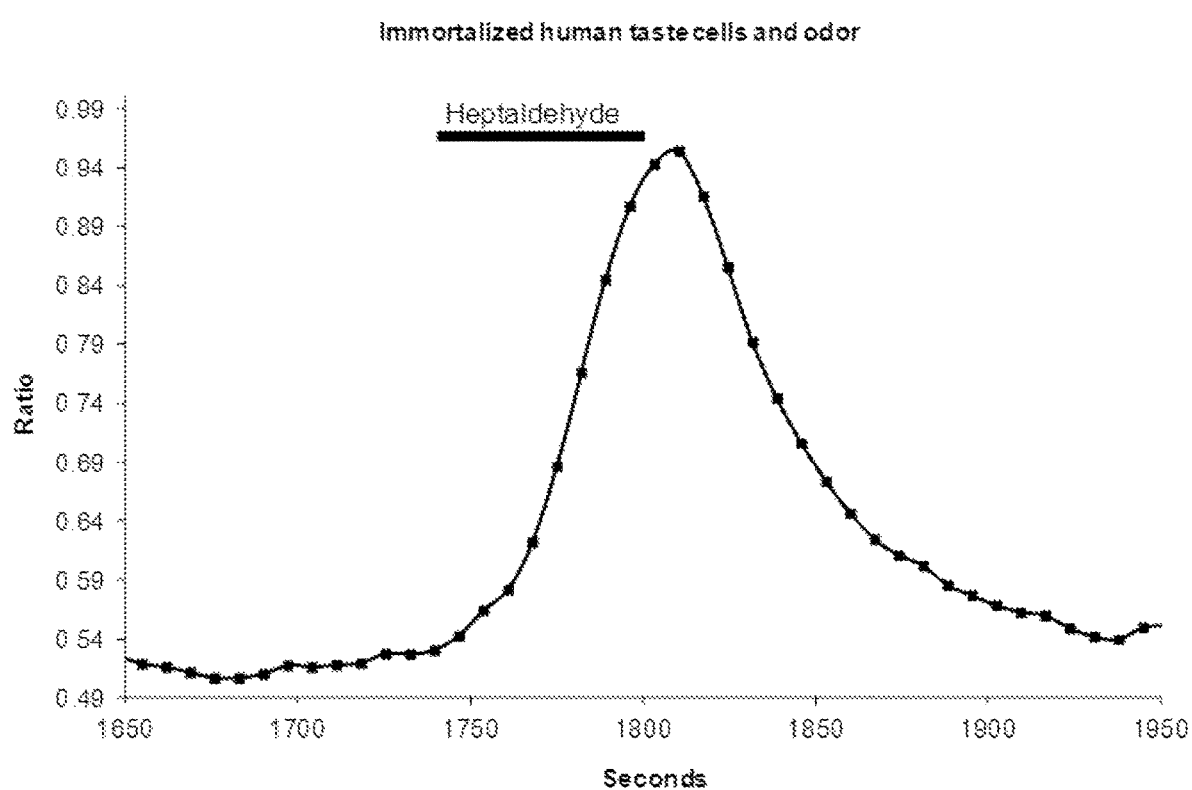
FIGS. 32A-32E demonstrate that immortalized human fungiform taste papillae cells respond to receptor specific odors as indicated the presence of specific odor receptors to heptaldehyde (32A), acetophenone (32B), methyl cinnamon (32C), eugenol (32D) and lyral (32E). Immortalized human fungiform taste papillae cells were obtained by immortalization of cultured human fungiform taste papillae (HBO) cells. These results demonstrated that immortalized human fungiform taste papillae cells preserve its original physiological and molecular and signal transduction properties.
Figure 32B:
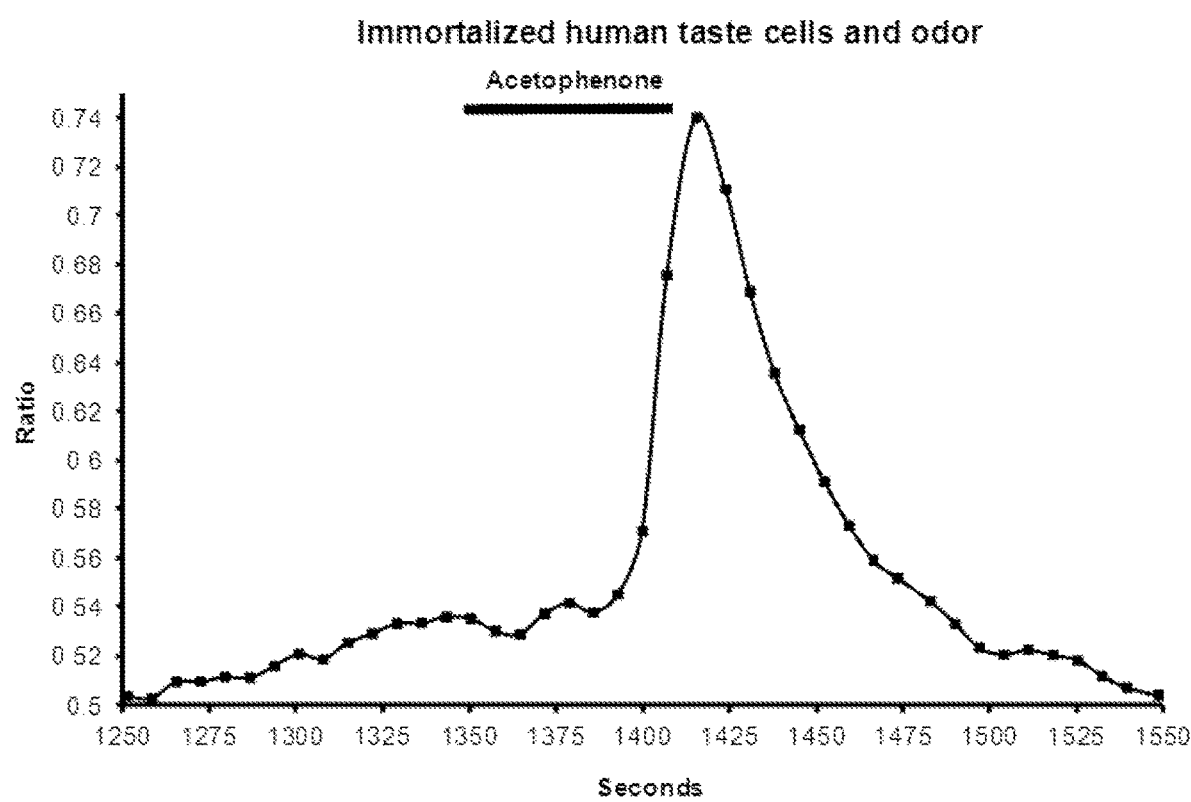
Figure 32C:
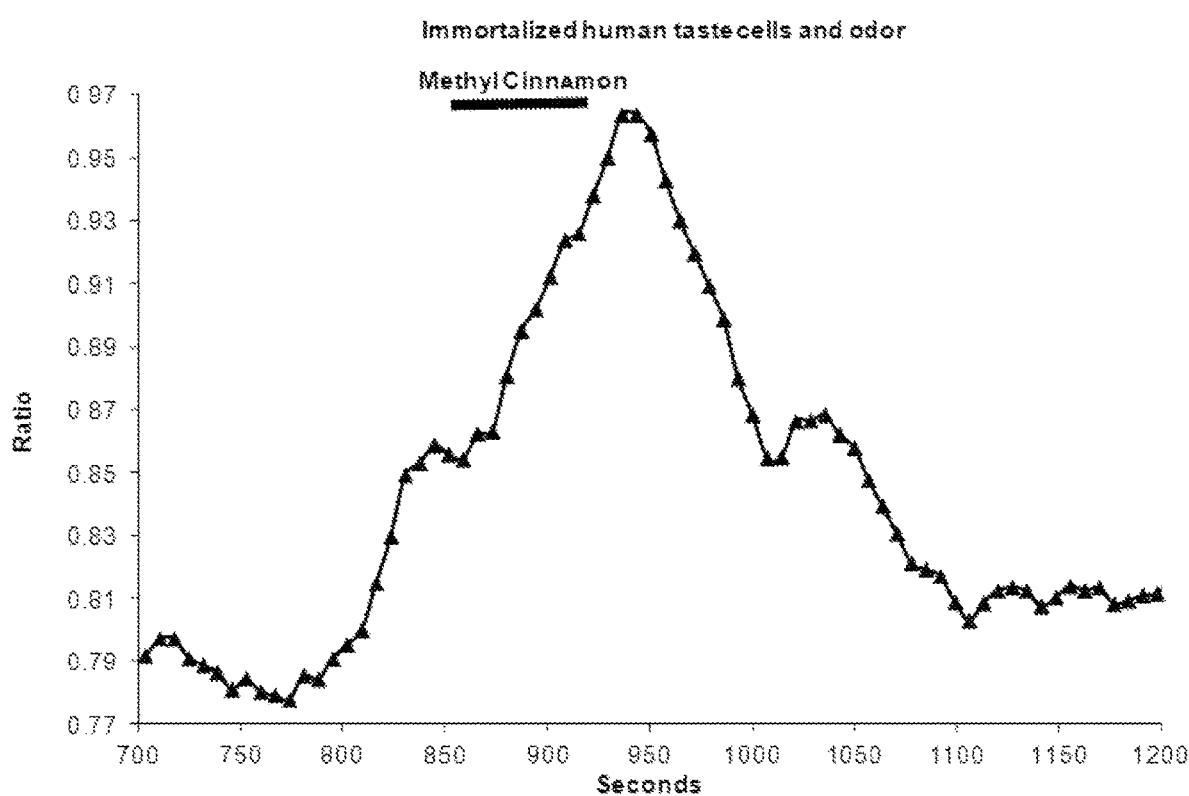
Figure 32D:
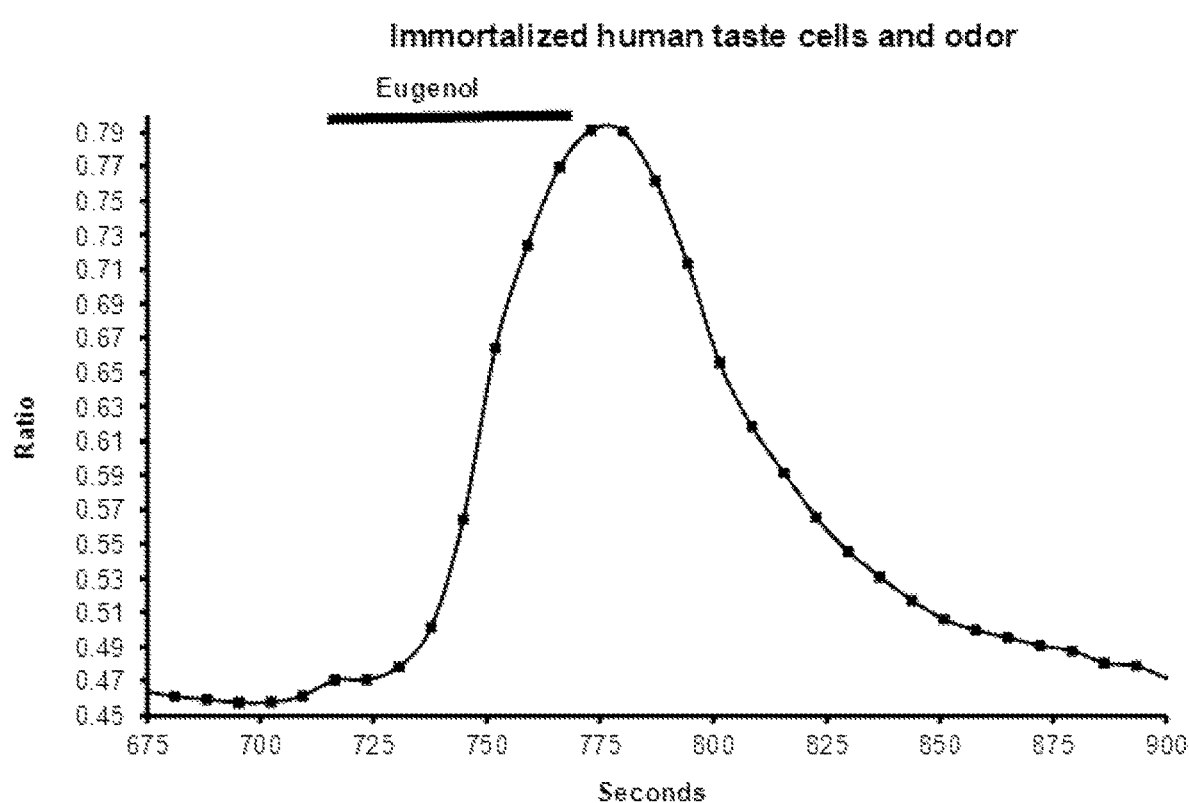
Figure 32E:
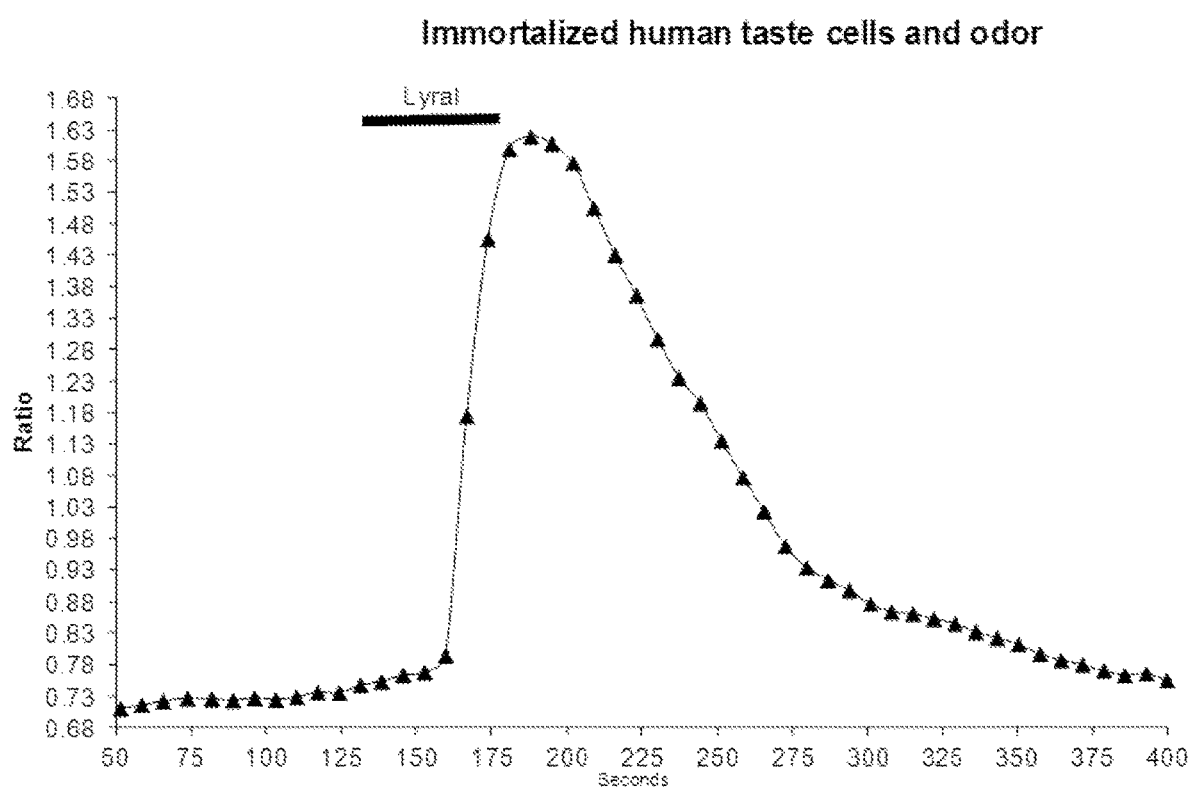

In one study, cultured human human taste (HBO) cells were transfected with approximately 1.5 micrograms olfactory receptor DNA ORS6 (also Olfr544, GenBank Sequence. Reference NM_020289.2) with chaperone DNA (receptor transporter protein 1 short (RTP1S) and M3 (muscarinic acetylcholine receptor) and olfactory receptor OR240 (also OR7D4; GenBank No. NM_001005191.2) with Chaperone DNA (RTP1S and M3). The Chaperone DNA is identified in Wu 2012 cited above. Transfection was performed using Lipofectamine 2000 reagent according to manufacturer's suggestions. After overnight incubation, the medium was changed for an additional 24 hours followed by manual calcium imaging using receptor specific odors, e.g., Androstanone, specific for OR 7D4/240 and Nonanedionic acid, a specific odor for S6. See FIGS. 31A and 31B. Although not depicted, response occurred at 30 or 100 micromolar concentrations.

In a similar manner, immortalized human fungiform taste papillae (Ulduz) cells, responded to receptor specific odors, heptaldehyde, acetophenone, methyl cinnamon, eugenol and lyral. See FIGS. 32A-32E.

All publications cited in this specification, and particularly U.S. provisional patent application No. 61/916,423, filed Dec. 16, 2013, are incorporated herein by reference. While the invention has been described with reference to particular embodiments, it will be appreciated that modifications can be made without departing from the spirit of the invention. Such modifications are intended to fall within the scope of the appended claims.

The invention claimed is:

1. A primary or immortalized mammalian taste papillae cell, taste cell line or taste cell membrane obtained therefrom comprising
    (a) a native functional taste receptor and chaperone or accessory proteins native to the cell;
    (b) a heterologous functional olfactory receptor (OR); and
    (c) a reporting agent that responds to activation of either said native taste cell receptor or the heterologous olfactory receptor.

2. The taste cell, taste cell line or taste cell membrane of claim 1, further comprising (d) an olfactory receptor which is native to the cell.

3. The taste cell, taste cell line or taste cell membrane of claim 1, further comprising multiple heterologous olfactory receptors and multiple endogenous olfactory receptors.

4. The taste cell, taste cell line or membrane according to claim 1, wherein said reporting agent is responsive to intracellular changes when said cells or membranes are contacted with a test agent that activates the OR.

5. The taste cell, taste cell line or membrane according to claim 4, wherein the reporting agent is a florescence resonance energy transfer system, a calcium sensitive indicator, a chloride-sensitive indicator, a potassium-sensitive indicator, a sodium-sensitive indicator, or a pH sensitive indicator.

6. The taste cell, taste cell line or membrane according to claim 1, which is modified to contain a gene encoding said reporting agent operably linked to a promoter.

7. The taste cell, taste cell line or membrane according to claim 6, wherein the reporting agent is glutathione-S-transferase (GST), c-myc, 6-histidine (6xHis), green fluorescent protein (GFP), maltose binding protein (MBP), influenza A virus haemagglutinin (HA), β-galactosidase, or GAL4).

8. The taste cell, taste cell line or membrane according to claim 1, wherein said heterologous OR uses the native chaperone or accessory proteins to facilitate the heterologous OR signal transduction cascade in response to activation of the heterologous OR by odor molecules.

9. The taste cell, taste cell line or taste cell membrane obtained therefrom according to claim 6, wherein the cells contain transiently transfected heterologous OR DNA operably linked to a suitable promoter.

10. The taste cell, taste cell line or taste cell membrane of claim 1, wherein said olfactory receptor is a mammalian olfactory receptor.

11. The taste cell, taste cell line or taste cell membrane of claim 10, wherein said olfactory receptor is a human olfactory receptor or a murine olfactory receptor.

12. A kit for identifying an agent as an odorant or a blocker or enhancer of an olfactory receptor ligand, said kit comprising: a mammalian taste papillae cell, taste cell line or cell membrane according to claim 1, a test agent, and instructions.

13. The kit of claim 12, further comprising a reporting agent that enables detection of activity of said olfactory receptor in response to said agent or a known odorant.

14. A method of identifying a modulator of an olfactory receptor, said method comprising:
    detecting the activity of said olfactory receptor of a mammalian taste papillae cell, taste cell line or taste cell membrane of claim 1, in the presence and absence of a test agent; and
    identifying said test agent as a modulator of the olfactory receptor if the receptor activity increases or decreases in the presence of said test agent relative to the activity of the olfactory receptor in the absence of said test agent.

15. The method of claim 14 wherein said step of detecting the activity of said olfactory receptor in the presence of said test agent comprises:
   (a) contacting said taste papillae cell or said taste papillae cell membrane with said test agent; and
   (b) determining intracellular $Ca^{2+}$ levels or cAMP levels; or
   (c) detecting a reporting agent or detecting a reporting agent of luciferase.

16. The method of claim 15, wherein said test agent is a natural agent, a synthetic agent, or an odiferous molecule.

17. A method for identifying an enhancer or blocker of an olfactory receptor ligand, comprising:
   (a) contacting a mammalian taste papillae cell, taste cell line or taste cell membrane of claim 1, with a test agent in the presence of said olfactory receptor ligand; and
   (b) detecting the activity of said olfactory receptor in the presence and absence of said test agent,
   wherein said test agent is an enhancer of said olfactory receptor ligand if the activity of said olfactory receptor in the presence of said test agent is increased relative to the activity of said olfactory receptor in the absence of said test agent; and
   wherein said test agent is a blocker of said olfactory receptor ligand if the activity of said olfactory receptor in the presence of said test agent is decreased relative to the activity of said olfactory receptor in the absence of said test agent.

18. An assay system comprising one or more primary or immortalized mammalian taste papillae cell, taste cell line or taste cell membrane obtained therefrom, wherein each said cell, cell line or cell membrane comprises
   (a) a native functional taste receptor and its chaperone or accessory proteins native to the cell;
   (b) a heterologous functional olfactory receptor (OR); and
   (c) a reporting agent that responds to activation of either said native taste cell receptor or the heterologous olfactory receptor,
   wherein said heterologous OR uses the native chaperone or accessory protein to facilitate the heterologous OR signal transduction cascade in response to activation of the heterologous OR by odor molecules.

* * * * *